US012611096B2

(12) United States Patent
Fridman

(10) Patent No.: US 12,611,096 B2
(45) Date of Patent: Apr. 28, 2026

(54) MINIMALISTIC INTRAORAL SCANNING SYSTEM

(71) Applicant: Align Technology, Inc., San Jose, CA (US)

(72) Inventor: Edi Fridman, Rishon le Zion (IL)

(73) Assignee: Align Technology, Inc., San Jose, CA (US)

( * ) Notice: Subject to any disclaimer, the term of this patent is extended or adjusted under 35 U.S.C. 154(b) by 251 days.

(21) Appl. No.: 18/216,554

(22) Filed: Jun. 29, 2023

(65) Prior Publication Data

US 2024/0023800 A1    Jan. 25, 2024

Related U.S. Application Data

(60) Provisional application No. 63/391,656, filed on Jul. 22, 2022.

(51) Int. Cl.
| | |
|---|---|
| *A61B 1/24* | (2006.01) |
| *A61B 1/00* | (2006.01) |
| *A61C 9/00* | (2006.01) |
| *A61C 13/34* | (2006.01) |
| *G06T 7/11* | (2017.01) |

(52) U.S. Cl.
CPC ............ *A61B 1/24* (2013.01); *A61B 1/00016* (2013.01); *A61B 1/00045* (2013.01); *A61B 1/00172* (2013.01); *A61C 9/0053* (2013.01); *A61C 13/34* (2013.01); *G06T 7/11* (2017.01); *A61B 1/0004* (2022.02); *G06T 2207/10028* (2013.01); *G06T 2207/20081* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 6,099,314 A | 8/2000 | Kopelman et al. | |
| 6,149,063 A * | 11/2000 | Reynolds ........... | G06K 17/0022 |
| | | | 235/472.01 |
| 6,334,772 B1 | 1/2002 | Taub et al. | |
| 6,334,853 B1 | 1/2002 | Kopelman et al. | |
| 6,463,344 B1 | 10/2002 | Pavlovskaia et al. | |
| 6,542,249 B1 | 4/2003 | Kofman et al. | |
| 6,614,206 B1 * | 9/2003 | Wong ................... | H02J 7/0042 |
| | | | 320/135 |

(Continued)

OTHER PUBLICATIONS

Co-pending U.S. Reissue U.S. Appl. No. 16/784,493, inventor Babayoff; Noam, filed Feb. 7, 2020.

(Continued)

*Primary Examiner* — Helen Zong
(74) *Attorney, Agent, or Firm* — Lowenstein Sandler LLP

(57) ABSTRACT

In embodiments set forth herein, an intraoral scanning system includes an intraoral scanner and a cradle and/or charging station for the intraoral scanner. The intraoral scanner generates intraoral scans and two-dimensional (2D) images during scanning, where the 2D images are generated according to a first frame rate. The intraoral scanner sends the intraoral scanner and the 2D images to the cradle. The cradle stores the intraoral scans and outputs a subset of the 2D images to a display according to a second frame rate that is lower than the first frame rate.

21 Claims, 13 Drawing Sheets

(56) References Cited

U.S. PATENT DOCUMENTS

| | | | |
|---|---|---|---|
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,683,865 B2 * | 3/2010 | Oh | G06F 1/1632 |
| | | | 345/905 |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Ampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 2018/0307953 A1 * | 10/2018 | Suzuki | G06K 15/1865 |
| 2018/0333232 A1 * | 11/2018 | Lee | A61B 1/24 |
| 2019/0388193 A1 | 12/2019 | Saphier et al. | |
| 2020/0100871 A1 * | 4/2020 | Wang | G06F 30/27 |
| 2020/0192488 A1 * | 6/2020 | Sabina | A61C 5/77 |
| 2020/0226896 A1 * | 7/2020 | Robertson | G06V 40/103 |
| 2020/0281702 A1 | 9/2020 | Avi et al. | |
| 2020/0336606 A1 | 10/2020 | Nagao | |
| 2021/0030503 A1 | 2/2021 | Shalev et al. | |
| 2021/0059796 A1 | 3/2021 | Weiss et al. | |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |
| 2021/0321872 A1 * | 10/2021 | Saphier | A61C 9/006 |
| 2023/0083575 A1 * | 3/2023 | Anderson | B25J 15/0052 |
| | | | 414/752.1 |
| 2023/0099970 A1 * | 3/2023 | Luo | G01S 7/52063 |
| | | | 600/443 |
| 2023/0132809 A1 * | 5/2023 | Kim | H04N 25/46 |
| | | | 348/207.99 |
| 2023/0306625 A1 * | 9/2023 | Peruch | G06K 7/1413 |
| 2023/0391017 A1 * | 12/2023 | Wucher | B33Y 50/02 |
| 2024/0078688 A1 * | 3/2024 | Jung | G06T 7/50 |
| 2024/0248209 A1 * | 7/2024 | Deng | G01S 17/89 |
| 2025/0120795 A1 * | 4/2025 | Fridman | A61B 1/00034 |
| 2025/0158276 A1 * | 5/2025 | Kim | A61B 1/00016 |

OTHER PUBLICATIONS

Co-pending U.S. Reissue U.S. Appl. No. 16/784,501, inventor Babayoff, Noam, filed Feb. 7, 2020.

Co-pending U.S. Reissue U.S. Appl. No. 16/784,515, inventor Babayoff, Noam, filed Feb. 7, 2020.

Co-pending U.S. Design U.S. Appl. No. 29/768,525, inventors Zakhar, Ginzburg et al., filed Jan. 29, 2021.

Co-pending U.S. Design U.S. Appl. No. 29/768,563, inventors Zakhar, Ginzburg et al., filed Jan. 29, 2021.

* cited by examiner

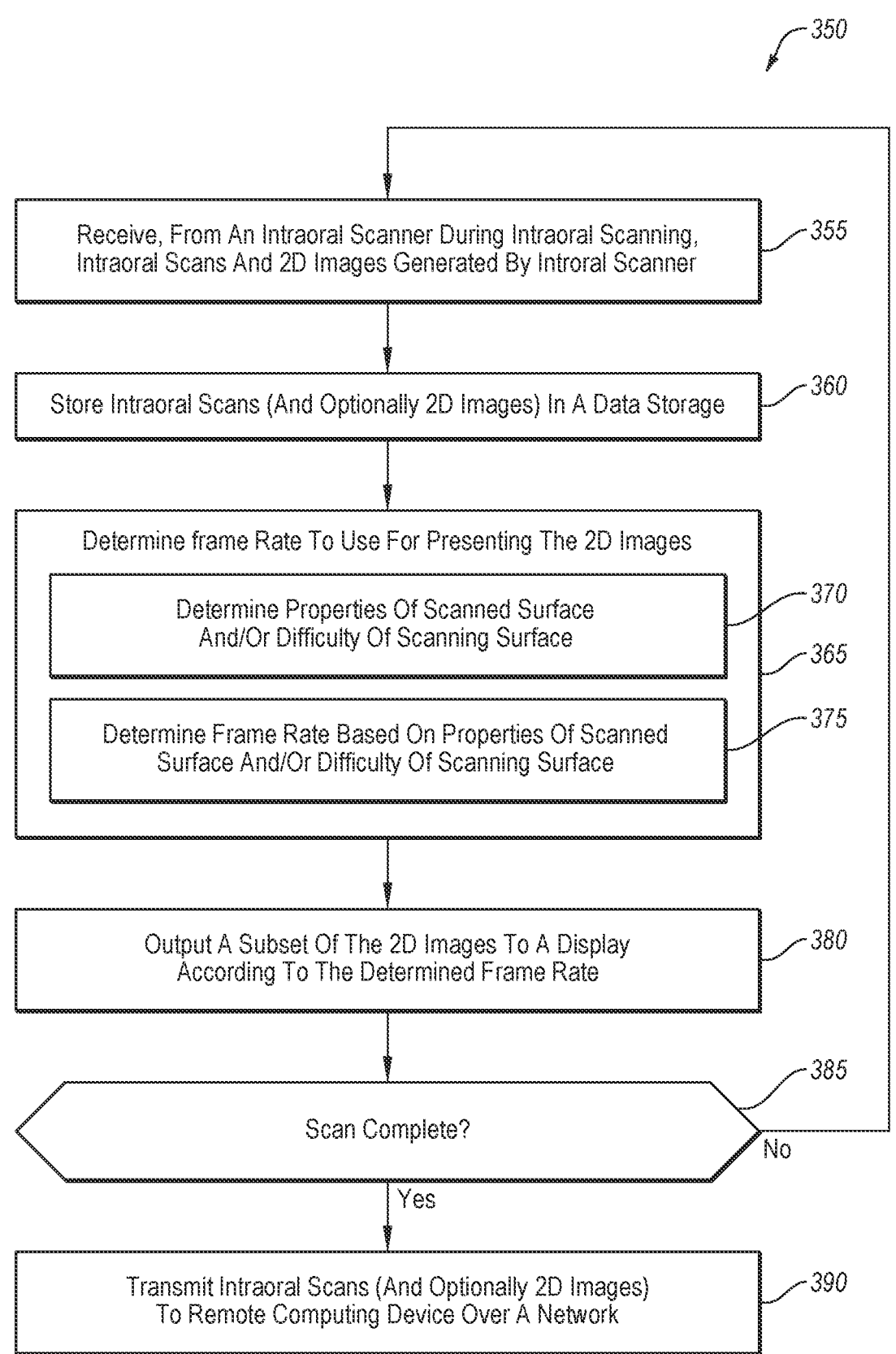

350

Receive, From An Intraoral Scanner During Intraoral Scanning, Intraoral Scans And 2D Images Generated By Introral Scanner — 355

Store Intraoral Scans (And Optionally 2D Images) In A Data Storage — 360

Determine frame Rate To Use For Presenting The 2D Images

Determine Properties Of Scanned Surface And/Or Difficulty Of Scanning Surface — 370

— 365

Determine Frame Rate Based On Properties Of Scanned Surface And/Or Difficulty Of Scanning Surface — 375

Output A Subset Of The 2D Images To A Display According To The Determined Frame Rate — 380

Scan Complete? — 385

No

Yes

Transmit Intraoral Scans (And Optionally 2D Images) To Remote Computing Device Over A Network — 390

FIG. 3B

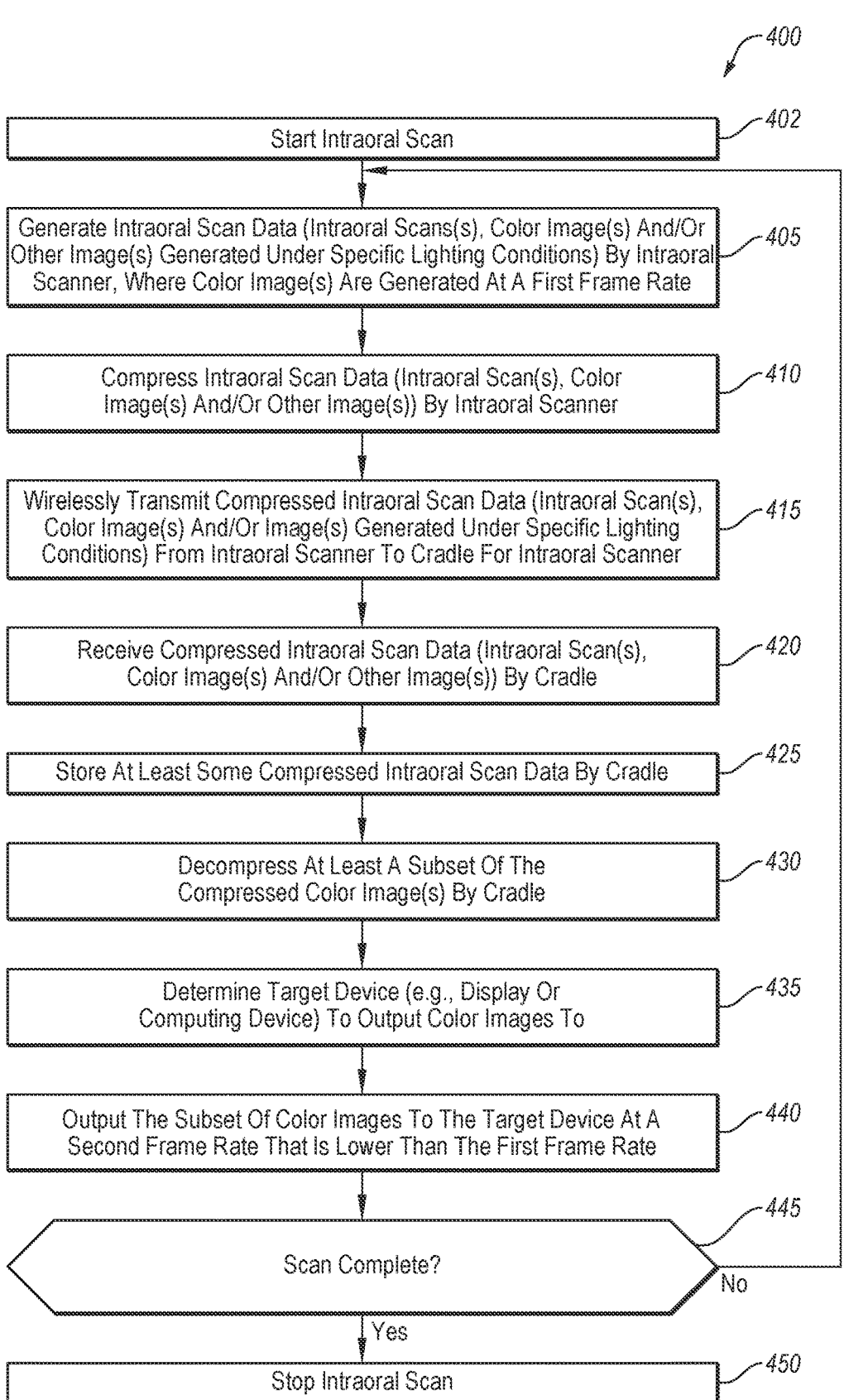

400

Start Intraoral Scan — 402

Generate Intraoral Scan Data (Intraoral Scans(s), Color Image(s) And/Or Other Image(s) Generated Under Specific Lighting Conditions) By Intraoral Scanner, Where Color Image(s) Are Generated At A First Frame Rate — 405

Compress Intraoral Scan Data (Intraoral Scan(s), Color Image(s) And/Or Other Image(s)) By Intraoral Scanner — 410

Wirelessly Transmit Compressed Intraoral Scan Data (Intraoral Scan(s), Color Image(s) And/Or Image(s) Generated Under Specific Lighting Conditions) From Intraoral Scanner To Cradle For Intraoral Scanner — 415

Receive Compressed Intraoral Scan Data (Intraoral Scan(s), Color Image(s) And/Or Other Image(s)) By Cradle — 420

Store At Least Some Compressed Intraoral Scan Data By Cradle — 425

Decompress At Least A Subset Of The Compressed Color Image(s) By Cradle — 430

Determine Target Device (e.g., Display Or Computing Device) To Output Color Images To — 435

Output The Subset Of Color Images To The Target Device At A Second Frame Rate That Is Lower Than The First Frame Rate — 440

Scan Complete? — 445

No

Yes

Stop Intraoral Scan — 450

*FIG. 4*

3D Rendering
Mode Virtual
Button
706

Touchscreen
706

Scanner
700

Previous
Segment
Virtual Button
710

Next
Segment
Virtual Button
712

3D Rendering Mode Virtual Button 706

Pan Virtual Button 722

Scanner 700

Rotate Virtual Button 724

Touchscreen 702

MINIMALISTIC INTRAORAL SCANNING SYSTEM

RELATED APPLICATIONS

This patent application claims the benefit under 35 U.S.C. § 119(e) of U.S. Provisional Application No. 63/391,656, filed Jul. 22, 2022, which is incorporated by reference herein.

TECHNICAL FIELD

Embodiments of the present disclosure relate to the field of dentistry and, in particular, to a minimalistic intraoral scanning system that includes a reduced number and simpler versions of components as compared to traditional intraoral scanning systems. Embodiments also relate to intraoral scanning systems that include wireless intraoral scanners

BACKGROUND

Intraoral scanning systems generally include an intraoral scanner, a costly computing device connected to the intraoral scanner via a wired connection for performing 3D rendering of intraoral scan data collected by the intraoral scanner, and a costly large display connected to the computing device via a wired conned for displaying the 3D rendering. The wired connection to the intraoral scanner provides power to the intraoral scanner and via the wired connection the computing device receives intraoral scan data from the intraoral scanner. The computing device processes the intraoral scan data and outputs a result of the processing to the display. Due to the cost of such intraoral scanning systems, it is often unfeasible for dentist offices in some areas such as in developing nations to invest in these intraoral scanning systems.

SUMMARY

In a $1^{st}$ implementation, an intraoral scanning system comprises: an intraoral scanner configured to generate intraoral scans and two-dimensional (2D) images during use; and a cradle for the intraoral scanner, the cradle comprising: a wireless module configured to wirelessly connect to the intraoral scanner; and a processing device to: receive the intraoral scans and the 2D images from the intraoral scanner; store the intraoral scans in data storage of the cradle; and output a subset of the 2D images to a display according to a first frame rate.

A $2^{nd}$ implementation may further extend the $1^{st}$ implementation. In the $2^{nd}$ implementation, the intraoral scanning system further comprises the display, wherein the display is one of a monitor, a television, a mobile device, or a desktop computer, and wherein the wireless module is to wirelessly connect with the display.

A $3^{rd}$ implementation may further extend the $1^{st}$ or $2^{nd}$ implementation. In the $3^{rd}$ implementation, the processing device is to receive the 2D images at a second frame rate that is greater than the first frame rate.

A $4^{th}$ implementation may further extend any of the $1^{st}$ through $3^{rd}$ implementations. In the $4^{th}$ implementation, the processing device is further to transmit the intraoral scans to a remote computing device via a network, wherein the remote computing device is to process the intraoral scans to generate a three-dimensional (3D) model of a patient's dental arch.

A $5^{th}$ implementation may further extend any of the $1^{st}$ through $4^{th}$ implementations. In the $5^{th}$ implementation, the first frame rate is a frame rate of about 1-10 frames per second.

A $6^{th}$ implementation may further extend any of the $1^{st}$ through $5^{th}$ implementations. In the $6^{th}$ implementation, the processing device is further to: receive a command to enter a local three-dimensional (3D) rendering mode; enter the local 3D rendering mode; and generate a 3D surface of a portion of a dental arch of a patient using a subset of the intraoral scans that is received after receipt of the command to enter the local 3D rendering mode.

A $7^{th}$ implementation may further extend the $6^{th}$ implementation. In the $7^{th}$ implementation, a size of the 3D surface is limited by a 3D bounding shape around the portion of the dental arch.

A n $8^{th}$ implementation may further extend any of the $6^{th}$ or $7^{th}$ implementations. In the $8^{th}$ implementation, the intraoral scanner comprises a touch screen, and wherein the touch screen is configured to present a virtual button that, when pressed, causes the command to enter the local 3D rendering mode to be sent to the processing device.

A $9^{th}$ implementation may further extend any of the $6^{th}$ through $8^{th}$ implementations. In the $9^{th}$ implementation, the processing device is further to: exit the local 3D rendering mode responsive to an exit criterion being satisfied; and discard the 3D surface of the portion of the dental arch responsive to exiting the local 3D rendering mode.

A $10^{th}$ implementation may further extend the $9^{th}$ implementation. In the $10^{th}$ implementation, the processing device is further to: determine at least one of a) a first amount of processing resources of the processing device that are being used or b) a second amount of the processing resources that are available; and determine that the exit criterion is satisfied responsive to at least one of a) the first amount of processing resources that are being used exceeding a first threshold or b) the second amount of processing resources that are available falling below a second threshold.

An $11^{th}$ implementation may further extend any of the $6^{th}$ rough $10^{th}$ implementations. In the $11^{th}$ implementation, the processing device or an additional processing device of the cradle is further to: segment the intraoral scans into hard tissue and soft tissue using one or more trained machine learning models; and discard a part of the intraoral scans identified as soft tissue to reduce a computational lode of generating the 3D surface of the portion of the dental arch.

A $12^{th}$ implementation may further extend the $11^{th}$ implementation. In the $12^{th}$ implementation, the processing device or the additional processing device is to use a trained machine learning model to segment the intraoral scans.

A $13^{th}$ implementation may further extend any of the $1^{st}$ through $12^{th}$ implementations. In the $13^{th}$ implementation, the processing device is further to adaptively change the first frame rate during intraoral scanning in accordance with a difficulty level associated with a portion of a dental arch being scanned.

A $14^{th}$ implementation may further extend the $13^{th}$ implementation. In the $14^{th}$ implementation, the processing device is to set the first frame rate to a first value responsive to determining that the portion of the dental arch is associated with a first difficulty level, and is to set the first frame rate to a second value that is lower than the first value responsive to determining that the portion of the dental arch is associated with a second difficulty level that is greater than the first difficulty level.

A $15^{th}$ implementation may further extend the $13^{th}$ or $14^{th}$ implementation. In the $15^{th}$ implementation, the processing device is to determine the difficulty level based on processing of at least one of a) one or more most recent intraoral scans or b) one or more most recent 2D images.

A 16$^{th}$ implementation may further extend the 15$^{th}$ implementation. In the 16$^{th}$ implementation, the processing is performed by inputting at least one of the one or more most recent intraoral scans or the one or more most recent 2D images into a trained machine learning model that outputs the difficulty level.

A 17$^{th}$ implementation may further extend any of the 1$^{st}$ through 16$^{th}$ implementations. In the 17$^{th}$ implementation, the cradle comprises an additional processing device optimized for executing one or more trained machine learning models, and wherein the additional processing device is to use the one or more trained machine learning models to process at least one of the intraoral scans or the 2D images to identify at least one of excess tissue, moving tissue, hard tissue, or soft tissue.

An 18$^{th}$ implementation may further extend any of the 1$^{st}$ through 17$^{th}$ implementations. In the 18$^{th}$ implementation, the processing device is further to: determine one or more properties of a surface being scanned; and adjust the first frame rate based on the one or more properties of the surface being scanned.

A 19$^{th}$ implementation may further extend any of the 1$^{st}$ through 18$^{th}$ implementations. In the 19$^{th}$ implementation, the intraoral scanner comprises a touch screen, and wherein the touch screen is configured to present one or more virtual buttons that, when pressed, causes a command to adjust the first frame rate to be adjusted.

A 20$^{th}$ implementation may further extend any of the 1$^{st}$ through 19$^{th}$ implementations. In the 20$^{th}$ implementation, the intraoral scanner comprises a touch screen, and wherein the touch screen is configured to present one or more virtual buttons that, when pressed, causes a command to select a static first frame rate or an adaptive first frame rate.

A 21$^{st}$ implementation may further extend any of the 1$^{st}$ through 20$^{th}$ implementations. In the 21$^{st}$ implementation, the cradle further comprises a display that is to display the subset of the 2D images.

A 22$^{nd}$ implementation may further extend the 21$^{st}$ implementation. In the 22$^{nd}$ implementation, the display comprises a touch screen.

In a 23$^{rd}$ implementation, a method of intraoral scanning comprises: generating, by an intraoral scanner, intraoral scans of a dental site and two-dimensional (2D) images of the dental site, wherein the 2D images are generated at a first frame rate; receiving, by a device wirelessly connected to the intraoral scanner, the intraoral scans and the 2D images; storing the intraoral scans in a data storage of the device; and outputting a subset of the 2D images to a display according to a second frame rate that is lower than the first frame rate.

A 24$^{th}$ implementation may further extend the 23$^{rd}$ implementation. In the 24$^{th}$ implementation, the display is one of a monitor, a television, a mobile device, or a desktop computer that is wirelessly connected to the device.

A 25$^{th}$ implementation may further extend the 23$^{rd}$ or 24$^{th}$ implementation. In the 25$^{th}$ implementation, the device is a cradle for the intraoral scanner.

A 26$^{th}$ implementation may further extend the 23$^{rd}$ through 25$^{th}$ implementations. In the 26$^{th}$ implementation, the method further comprises: transmitting the intraoral scans from the device to a remote computing device via a network, wherein the remote computing device is to process the intraoral scans to generate a three-dimensional (3D) model of a patient's dental arch.

A 27$^{th}$ implementation may further extend the 23$^{rd}$ through 26$^{th}$ implementations. In the 27$^{th}$ implementation, the second frame rate is a frame rate of about 1-10 frames per second.

A 28$^{th}$ implementation may further extend the 23$^{rd}$ through 27$^{th}$ implementations. In the 28$^{th}$ implementation, the method further comprises: receiving, at the device, a command to enter a local three-dimensional (3D) rendering mode; entering the local 3D rendering mode; and generating a 3D surface of a portion of a dental arch of a patient using only a subset of the intraoral scans that is received after receiving the command to enter the local 3D rendering mode.

A 29$^{th}$ implementation may further extend the 28$^{th}$ implementation. In the 29$^{th}$ implementation, a size of the 3D surface is limited by a 3D bounding shape around the portion of the dental arch.

A 30$^{th}$ implementation may further extend the 28$^{th}$ or 29$^{th}$ implementation. In the 30$^{th}$ implementation, the intraoral scanner comprises a touch screen, the method further comprising: presenting, via the touch screen, a virtual button associated with the local 3D rendering mode; receiving user interaction with the virtual button; and sending the command to enter the local 3D rendering mode from the intraoral scanner to the device.

A 31$^{st}$ implementation may further extend the 28$^{th}$ rough 30$^{th}$ implementations. In the 31$^{st}$ implementation, the method further comprises: determining that an exit criterion for exiting the local 3D rendering mode is satisfied; exiting the local 3D rendering mode; and discarding the 3D surface of the portion of the dental arch responsive to exiting the local 3D rendering mode.

A 32$^{nd}$ implementation may further extend the 31$^{st}$ implementation. In the 32$^{nd}$ implementation, the method further comprises: determining at least one of a) a first amount of processing resources of the processing device that are being used or b) a second amount of the processing resources that are available; and determining that the exit criterion is satisfied responsive to at least one of a) the first amount of processing resources that are being used exceeding a first threshold or b) the second amount of processing resources that are available falling below a second threshold.

A 33$^{rd}$ implementation may further extend the 28$^{th}$ rough 32$^{nd}$ implementations. In the 33$^{rd}$ implementation, the method further comprises: Inputting the intraoral scans into a one or more trained machine learning models, wherein the one or more trained machine learning models generate an output segmenting the intraoral scans into hard tissue and soft tissue; and discarding a part of the intraoral scans, wherein the discarded part of the intraoral scans is not used for generating the 3D surface of the portion of the dental arch.

A 34$^{th}$ implementation may further extend the 23$^{rd}$ through 33$^{rd}$ implementations. In the 34$^{th}$ implementation, the method further comprises: adaptively changing the second frame rate during intraoral scanning in accordance with a difficulty level associated with a portion of a dental arch being scanned.

A 35$^{th}$ implementation may further extend the 34$^{th}$ implementation. In the 35$^{th}$ implementation, the method further comprises: setting the second frame rate to a first value responsive to determining that the portion of the dental arch is associated with a first difficulty level; and setting the second frame rate to a second value that is lower than the first value responsive to determining that the portion of the dental arch is associated with a second difficulty level that is greater than the first difficulty level.

A 36$^{th}$ implementation may further extend the 35$^{th}$ implementation. In the 36$^{th}$ implementation, the method further comprises: determining the difficulty level based on processing of at least one of a) one or more most recent intraoral scans or b) one or more most recent 2D images.

A 37$^{th}$ implementation may further extend the 36$^{th}$ implementation. In the 37$^{th}$ implementation, the processing is performed by inputting at least one of the one or more most recent intraoral scans or the one or more most recent 2D images into a trained machine learning model that outputs the difficulty level.

A 38$^{th}$ implementation may further extend any of the 23$^{rd}$ through 37$^{th}$ implementations. In the 38$^{th}$ implementation, the method further comprises: inputting at least one of the intraoral scans or the 2D images into the one or more trained machine learning models, wherein the one or more trained machine learning models generate an output identifying at least one of excess tissue, moving tissue, hard tissue, or soft tissue.

A 39$^{th}$ implementation may further extend any of the 23$^{rd}$ through 38$^{th}$ implementations. In the 39$^{th}$ implementation, the method further comprises: determining one or more properties of a surface being scanned; and adjusting the first frame rate based on the one or more properties of the surface being scanned.

A 40$^{th}$ implementation may further extend any of the 23$^{rd}$ through 39$^{th}$ implementations. In the 40$^{th}$ implementation, the intraoral scanner comprises a touch screen, the method further comprising: displaying, via the touch screen, one or more virtual buttons that, when pressed, causes a command to adjust the second frame rate to be adjusted; receiving a user interaction with at least one of the one or more virtual buttons; generating a command to adjust the second frame rate; and sending the command from the intraoral scanner to the device.

A 41$^{st}$ implementation may further extend any of the 23$^{rd}$ through 40$^{th}$ implementations. In the 41$^{st}$ implementation, the intraoral scanner comprises a touch screen, the method further comprising: displaying, via the touch screen, one or more virtual buttons that, when pressed, causes a command to select a static second frame rate or an adaptive second frame rate; receiving a user interaction with at least one of the one or more virtual buttons; generating a command to select the static second frame rate or the static second frame rate based on the user interaction with the at least one of the one or more virtual buttons; and sending the command from the intraoral scanner to the device.

A 42$^{nd}$ implementation may further extend any of the 23$^{rd}$ through 41$^{st}$ implementations. In the 42$^{nd}$ implementation, a computer readable medium comprises instructions that, when executed by a processing device, cause the processing device to perform the operations of any of the 23$^{rd}$ through the 41$^{st}$ implementations.

BRIEF DESCRIPTION OF THE DRAWINGS

Embodiments of the present disclosure are illustrated by way of example, and not by way of limitation, in the figures of the accompanying drawings.

FIG. 3B illustrates a flow diagram for a method of processing intraoral scans using an intraoral scanning system, in accordance with an embodiment.

FIG. 4 illustrates a flow diagram for a method of processing intraoral scans using an intraoral scanning system, in accordance with an embodiment.

DETAILED DESCRIPTION

Figure 1A:
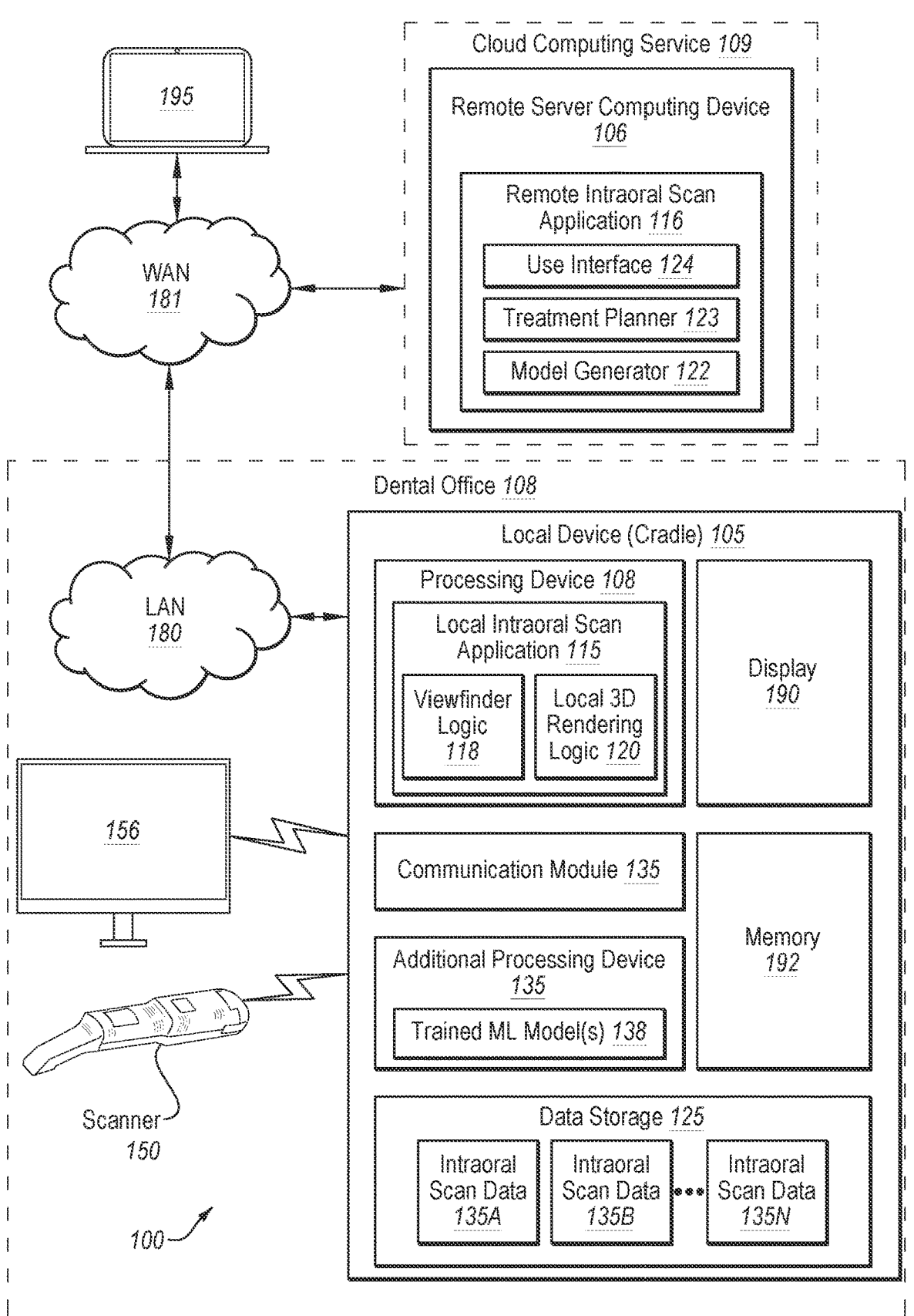
FIG. 1A illustrates a minimalistic intraoral scanning, in accordance with an embodiment.

Described herein are embodiments of a simplified or minimalistic intraoral scanning system that is lower cost and/or that has fewer components than traditional intraoral scanning systems. In embodiments, the intraoral scanning system includes an intraoral scanner connected to a local device such as a cradle and/or charging station for the intraoral scanner via a wired or wireless connection. The local device may include a processing device and/or storage for receiving and storing intraoral scan data generated by the intraoral scanner. The local device may additionally output images (e.g., two-dimensional (2D) images) generated by the intraoral scanner to a display. The display may be component of the local device, may be connected to the local device via a wired connection, or may be connected with the local device via a wireless connection. The intraoral scanner may generate the images at a first refresh rate, and the local device may output the images to a display at a second refresh rate that is lower than the first refresh rate in some embodiments.

Conventional intraoral scanning systems include a dedicated computing platform that has sufficient computational resources to process intraoral scans and generate a 3D surface from the intraoral scans as those intraoral scans are generated by the intraoral scanner. Such conventional intraoral scanning systems additionally include a large display in order to display the 3D surface. This enables a doctor to view the 3D surface of a patient's dental arch in real time or near-real time during intraoral scanning. Accordingly, the doctor can know what regions of the dental arch still need to be scanned, can know which regions of the dental arch need additional data, and so on. While the dedicated computing platform and large display of conventional intraoral scanning systems are beneficial to some doctors, other doctors may not have the funds to afford such conventional intraoral scanning systems.

Embodiments provide a lower cost intraoral scanning system that includes an intraoral scanner and a cradle or other device that has sufficient computational power to communicate with the intraoral scanner, store and transmit intraoral scans, and receive and output to a display 2D images. Notably, the lower cost intraoral scanning system of embodiments herein may not have sufficient computational power to generate 3D surfaces of full dental arches. Instead, the intraoral scanning system may offload the generation of such 3D surfaces and 3D models to a remote computing device, such as a server running in a cloud.

It can be important in embodiments for the generated intraoral scan data to be sufficiently plentiful for all regions of a dental arch to enable a high quality 3D model to be generated of that dental arch. However, since 3D surfaces and 3D models may not be generated by the intraoral scanning system during intraoral scanning, it is useful for the intraoral scanning system to have some mechanism to ensure that sufficient data is collected for each portion of the dental site. In some embodiments, the intraoral scanning system controls a refresh rate at which images (e.g., color 2D images referred to as viewfinder images) are displayed during intraoral scanning. Users of the intraoral scanning system naturally move the intraoral scanner at a speed commensurate with the refresh rate. If the refresh rate slows down, then a user assumes that the speed at which the intraoral scanner is moved during scanning should also slow down. Users may also be instructed (e.g., by the intraoral scanning system and/or a user manual) that scanning speed (e.g., speed at which the intraoral scanner is moved during scanning) should be about the same as or slower than the refresh rate. For difficult to scan areas the refresh rate at which 2D images are output to a display may be slowed down, and for easy to scan areas the refresh rate may be sped up. Alternatively, a static refresh rate may be used that is sufficiently slow to gather at least a minimum amount of data for both easy to scan and difficult to scan regions. In this manner, the scanning system may ensure that sufficient intraoral scans are collected for generation of a high quality three-dimensional (3D) model while foregoing expensive components such as a dedicated powerful computing platform and a large display. In embodiments, the cost of the intraoral scanning system is below $1000 or even below $600 or $500, as opposed to the cost of conventional intraoral scanning systems which can be thousands to tens of thousands of dollars.

Various embodiments are described herein. It should be understood that these various embodiments may be implemented as stand-alone solutions and/or may be combined. Accordingly, references to an embodiment, or one embodiment, may refer to the same embodiment and/or to different embodiments. Some embodiments are discussed herein with reference to intraoral scans and intraoral images. However, it should be understood that embodiments described with reference to intraoral scans also apply to lab scans or model/impression scans. A lab scan or model/impression scan may include one or more images of a dental site or of a model or impression of a dental site, which may or may not include height maps, and which may or may not include color images.

FIG. 1A illustrates an intraoral scanning system 100, in accordance with an embodiment. Intraoral scanning system 100 may include only components located at a single location (e.g., at a dentist office 108 or a dental lab) in embodiments. The intraoral scanning system 100 may be a low cost minimalistic intraoral scanning system that offloads some portion of operations (e.g., image processing and 3D model generation) to a remote server computing device 106 (e.g., which may execute as part of a cloud computing service 109). The intraoral scanning system at a minimum includes an intraoral scanner (also referred to simply as a scanner) 150 and a local device 105, which may be a cradle and/or charging station for the intraoral scanner 150 in embodiments. In some embodiments, the intraoral scanning system 100 may additionally include, or take advantage of, a display 156 and/or a local area network (LAN) 180. Via the LAN 180, the intraoral scanning system 100 (e.g., the local device 105) may connect to a wide area network (WAN) 181, and through the WAN 181 to a remote server computing device 106. The LAN 180 may include a router, switch, bridge and/or other network device (not shown) that enables communication between multiple devices (e.g., device 105 and scanner 150) connected to the LAN 180. The network device may provide wired connections to the LAN using, for example, Ethernet ports, universal serial bus (USB) ports and/or Firewire® ports. The network device may additionally provide wireless connections to the LAN using, for example, a Wi-Fi transceiver.

The WAN 181 may include a public WAN (e.g., the Internet), a private WAN (e.g., an intranet), or a combination thereof. The WAN 181 may include or connect to remote server computing device 106. The server computing device 106 may include a physical machine and/or a virtual machine hosted by a physical machine. The physical machine may be a rackmount server, a desktop computer, or other computing device. In one embodiment, the server computing device 106 includes a virtual machine managed and provided by a cloud provider system or cloud computing service 109. Each virtual machine offered by a cloud service provider may be hosted on a physical machine configured as part of a cloud. Such physical machines are often located in a data center. The cloud provider system and cloud may be provided as an infrastructure as a service (IaaS) layer. One example of such a cloud is Amazon's® Elastic Compute Cloud (EC2®).

In some embodiments, local device 105 connects to scanner 150 wirelessly via a wireless protocol. The connection may be an indirect connection via LAN 180 or may be a direct connection between local device 105 and scanner 150. For example, scanner 150 may pair with and communicate wirelessly with local device 105 using a wireless protocol.

In some embodiments, local device 105 may not support any of the communication types supported by the network device of the LAN 180. For example, device 105 may support Zigbee or Bluetooth, but may not support Wi-Fi. In such an embodiment, to enable device 105 to connect to the LAN 180, the LAN 180 may include a gateway device (not shown) connected to the network device via one of the connection types supported by the network device (e.g., via Ethernet or Wi-Fi). The gateway device may additionally support other communication protocols such as Zigbee, PLC and/or Bluetooth, and may translate between supported communication protocols. Accordingly, in some embodiments device 105 may connect to the LAN 180 through the gateway device.

Local device 105 may include a processing device 108, a communication module 135, a memory 192, and/or a data storage 125. In some embodiments, memory 192 and data storage 125 are combined. In some embodiments, the processing device 108, communication module 135, memory 192 and/or data storage 125 are components of a system on a chip (SoC).

The processing device 108 may be or include a microcontroller, a DSP, a PLC, a microprocessor or programmable logic device such as an FPGA or a CPLD. The processing device 108 may additionally or alternatively include one or more special purpose processor and/or general purpose processor, such as a complex instruction set computing (CISC) microprocessor, reduced instruction set computing (RISC) microprocessor, very long instruction word (VLIW) microprocessor, processor implementing other instruction sets, or processor implementing a combination of instruction sets. Examples of special-purpose processing devices include an application specific integrated circuit (ASIC), a field programmable gate array (FPGA), a digital signal processor (DSP), and network processor. Processing device 108 is configured to execute a local intraoral scan application 115 in embodiments.

The memory may include a non-volatile memory (e.g., RAM) and/or a volatile memory (e.g., ROM, Flash, etc.). The data storage 125 may include a local data store and/or a remote data store. The data storage 125 may be or include secondary storage, such as a disc drive, a solid state drive, and so on. Local device 105 may additionally include a display 190 and/or one or more additional processing device 135 in some embodiments.

The communication module 135 enables the device 105 to connect to a LAN and/or directly to other devices such as scanner 150. The communication module 135 may be configured to manage security, manage sessions, manage communications with external devices, and so forth. In one embodiment, the communication module 135 is configured to wirelessly communicate using Wi-Fi®. Alternatively, or additionally, the communication module may be configured to communicate using Bluetooth®, Zigbee®, Internet Protocol version 6 over Low power Wireless Area Networks (6LowPAN), power line communication (PLC), Ethernet (e.g., 10 Megabyte (Mb), 100 Mb and/or 1 Gigabyte (Gb) Ethernet) or other communication protocols.

In some embodiments, local device 105 includes one or more additional processing device 135. The additional processing device 135 may be a specialized processing device that is optimized for execution of trained machine learning models. Additional processing device 135 may execute one or more trained machine learning (ML) models 138, which may include models for identifying (e.g., on a point, patch or pixel level) moving tissue, foreign objects, excess tissue, soft tissue, hard tissue, and so on. Outputs of the trained machine learning model(s) 138 may be provided to local intraoral scan application 115, which may use such outputs to perform one or more actions. Examples of trained machine learning models 138 that may execute on the additional processing device 135 are described in U.S. Pat. No. 11,367,192, issued Jun. 21, 2022, and entitled "Foreign Object Filtering for Intraoral scanning" and U.S. Pat. No. 11,238,586, issued Feb. 1, 2022, and entitled "Excess Material Removal Using Machine learning, which are each incorporated by reference herein in their entirety.

In some embodiments, local device 105 is a device (e.g., a cradle and charger for an intraoral scanner) that includes an embedded system. An embedded system is a class of computing device that is embedded into another device as one component of the device. The device typically also includes other hardware, electrical and/or mechanical components that may interface with the embedded system. Embedded systems are typically configured to handle a particular task or set of tasks, for which the embedded systems may be optimized. Accordingly, the embedded systems may have a minimal cost and size as compared to general computing devices.

In one embodiment, local device 105 includes an embedded system that includes processing device 108, communication module 135, memory 192, additional processing device 135 and/or data storage 125. The embedded system may also include other components that are not shown herein. Examples of such additional components may include light emitting diodes (LEDs), a power supply regulator, fuses, ports, a user interface, digital to analog (D/A) converters, analog to digital (A/D) converters, field programmable gate arrays (FPGAs), application specific integrated circuits (ASICs), and so on.

In some embodiments, local device 105 includes a display 190. The display 190 may be an integrated or attached display 190. The display may alternatively be a wireless device that wirelessly connects to the local device 105. The display may be a relatively small display (e.g., 10" screen, 6" screen, or the like), and may include a touch screen in embodiments. In one embodiment, the local device 105 is a cradle that holds and charges both the intraoral scanner 150 and the display 190. In one embodiment, the local device 105 is a cradle for the intraoral scanner 150, and the display 190 is attached to the cradle via a rotatable joint. Accordingly, the display can be rotated so that it can be viewed by a doctor regardless of an orientation of the cradle.

In embodiments, intraoral scanner 150 is wirelessly connected to local device 105. In one embodiment, scanner 150 is wirelessly connected to device 105 via a direct wireless connection. In one embodiment, scanner 150 is wirelessly connected to device 105 via a wireless network (e.g., LAN 180). In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, local device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router.

In some embodiments, local device 105 connects to one or more displays 156. Examples of displays include televisions (e.g., smart TVs), computer monitors, mobile devices that include displays (e.g., mobile phones, laptop computers, tablet computers, etc.), augmented reality (AR) headsets, mixed reality (MR) headsets, and so on. Some displays 156 may be physically connected to the local device 105 via a wired connection. Some displays 156 may be wirelessly connected to device 105 via a wireless connection, which may be a direct wireless connection or a wireless connection via a wireless network. In embodiments, display 156 is a smart display such as a smart television (TV). A smart TV may include an application installed thereon for communicating with and/or acting as a remote display for device 105. Alternatively, or additionally, a smart TV may include a web browser, which may be used to navigate to a web page that streams data from device 105. For example, the web page may stream a user interface of local intraoral scan application 115.

Intraoral scanner 150 may be a wireless handheld device that is not tethered to a computer, display, and/or other hardware. Alternatively, intraoral scanner 150 may have a wired connection to device 105, a power adapter, a power box, and/or another device. Intraoral scanner 150 may include or be a probe (e.g., a hand held probe) for optically capturing three-dimensional structures. The intraoral scanner 150 may be used to perform intraoral scanning of a patient's oral cavity.

Intraoral scanner 150 may include one or more light source, optics and one or more detectors for generating intraoral scan data (e.g., intraoral scans, color images, NIRI images, etc.), one or more buttons and/or touch sensitive inputs (e.g., touch pads and/or touchscreens), and so on. Intraoral scanner 150 may additionally include a memory and/or a processing device (e.g., a controller) for performing initial processing on some or all of the intraoral scan data before it is transmitted to local server computing device 105. Scanner 150 may additionally include a communication module (e.g., a wireless communication module) such as a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols. Alternatively, the scanner 150 may connect to a wide area network (WAN) such as the Internet, and may connect to the local server computing device 105 and/or remote server computing device 106 via the WAN. One example of a scanner 150 is the iTero® intraoral digital scanner manufactured by Align Technology, Inc. Another example of a scanner 150 is set forth in U.S. Publication No. 2019/0388193, filed Jun. 19, 2019, which is incorporated by reference herein. Two example scanners are described in greater detail below with reference to FIGS. 9-10.

In embodiments, the scanner 150 may include a wireless communication module, one or more rechargeable battery, one or more replaceable battery (which may or may not be rechargeable), a charging module for charging the one or more rechargeable battery and/or a controller (e.g., a processing device) for controlling one or more functions of the scanner 150, among many other components, some of which are discussed herein below.

In addition to or instead of including a wireless communication module, scanner 150 may include an Ethernet network interface controller (NIC), a universal serial bus (USB) port, a parallel port, a serial port, or other wired port. In some embodiments, the NIC or port may connect the scanner 150 to a device 105 via a wired connection.

Intraoral scanner 150 may generate intraoral scans, which may be or include color or monochrome 3D information, and send the intraoral scans to local server computing device 105 via the wireless connection. In some embodiments, intraoral scans include height maps. Intraoral scanner 150 may additionally or alternatively generate color two-dimensional (2D) images (e.g., viewfinder images), and send the color 2D images to local server computing device 105 via the wireless connection. Scanner 150 may additionally or alternatively generate 2D or 3D images under certain lighting conditions, such as under conditions of infrared or near-infrared (NIRI) light and/or ultraviolet light, and may send such 2D or 3D images to server computing device 105 via the wireless connection. Intraoral scans, color images, and images under specified lighting conditions (e.g., NIRI images, infrared images, ultraviolet images, etc.) are collectively referred to as intraoral scan data 135A-N. An operator may start recording scans with the scanner 150 at a first position in the oral cavity, move the scanner 150 within the oral cavity to a second position while the scans are being taken, and then stop recording the scans. In some embodiments, recording may start automatically as the scanner 150 identifies teeth and/or other objects.

A local intraoral scan application 115 running on processing device 108 of device 105 may wirelessly communicate with the scanner 150 via communication module 135 to effectuate an intraoral scan. A result of the intraoral scan may be intraoral scan data 135A, 135B through 135N that may include one or more sets of intraoral scans, one or more sets of viewfinder images (e.g., color 2D images showing a field of view of the intraoral scanner), one or more sets of NIRI images, and so on. Each intraoral scan may be a two-dimensional (2D) or 3D image that includes a height information (e.g., a height map) of a portion of a dental site, and thus may include x, y and z information. In one embodiment, each intraoral scan is a point cloud. In one embodiment, the intraoral scanner 150 generates numerous discrete (i.e., individual) intraoral scans and/or additional images. In some embodiments, sets of discrete intraoral scans may be merged into a smaller set of blended intraoral scans, where each blended scan is a combination of multiple discrete intraoral scans.

In embodiments, scanner 150 generates and sends to device 105 a stream of intraoral scan data. The stream of intraoral scan data may include separate streams of intraoral scans, color images and/or NIRI images (and/or other images under specific lighting conditions) in some embodiments. In one embodiment, a stream of blended intraoral scans is sent to computing device 105. In embodiments, the color 2D images in the stream are generated at a first frame rate.

In some embodiments, scanner 150 compresses intraoral scan data (e.g., intraoral scans, color images, NIRI images, etc.) prior to sending the intraoral scan data to device 105. In some embodiments, video compression techniques (e.g., optionally based on H.264 codec) are used to compress the stream of intraoral scan data. In some embodiments, intraoral scan data is compressed by a factor of 20 to 40. Accordingly, similarities between sequentially generated scans/images may be used to reduce the amount of data sent for each scan/image. For example, scanner 150 may determine a delta or difference between a previously sent scan and a current scan, and may send over the delta or difference rather than the scan or image. This may significantly reduce an amount of information sent over the wireless connection. Scanner 150 may include an onboard (e.g., internal) processing device that performs compression of at least some of the intraoral scan data.

In some embodiments, scanner 150 does not send whole scans and/or whole images to device 105. In one embodiment, scanner 150 may perform one or more computations on the intraoral scan data (e.g., intraoral scans, color images, NIRI images, etc.) to determine one or more areas of interest (AOIs) within the intraoral scan data. The one or more computations may be performed using trained machine learning models that are optimized for resource constrained devices and/or using one or more image processing algorithms. Scanner 150 may then perform data reduction such as by cropping the intraoral scans, images, etc. such that areas outside of the AOIs are cropped out of the scans/images and/or by reducing a resolution of areas outside of the AOIs. Scanner 150 may include an onboard processing device that can perform the one or more computations and/or data reduction/cropping of the scan data. The cropped or reduced scans/images are then sent to computing device 105. This, in addition to or instead of performing compression on the intraoral scan data, can reduce a total bandwidth associated with sending intraoral scan data to local server computing device 105. In one embodiment, AOIs are determined for intraoral scans, and intraoral scans are cropped or reduced before sending to computing device 105, but whole color images such as color viewfinder images are sent to computing device 105 without first cropping or reducing the color images. The uncropped viewfinder image may be presented to a doctor/dentist during the scanning process to show a current field of view of the scanner 150.

Local device 105 receives intraoral scan data from scanner 150, then stores the intraoral scan data 135A-N in data storage 125. If the intraoral scan data has been compressed, computing device 105 may decompress the intraoral scan data before it is stored. Alternatively, computing device 105 may store the intraoral scan data in a compressed state, and may decompress the intraoral scan data before processing it. In some embodiments, only some of the intraoral scan data is stored (e.g., just the intraoral scans may be stored).

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan/image data sets, each of which may include 2D intraoral scans/images and/or 3D intraoral scans/images of particular teeth and/or regions of an intraoral site. In one embodiment, separate scan/image data sets are created for the maxillary arch, for the mandibular arch, for a patient bite, and for each preparation tooth. Alternatively, a single large intraoral scan/image data set is generated (e.g., for a mandibular and/or maxillary arch). Such scans/images may be provided from the scanner to the device 105 in the form of one or more points (e.g., one or more pixels and/or groups of pixels). For instance, the scanner 150 may provide such a 3D scan/image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

During an intraoral scan session, local intraoral scan application 115 receives intraoral scan data including intraoral scans and 2D images such as color 2D images (e.g., viewfinder images) and near infrared (NIRI) images. Local intraoral scan application 115 stores at least a portion of the intraoral scan data 135A, 135B through 135N (e.g., just the intraoral scans or the intraoral scans plus 2D images) in data storage 125. Depending on a currently active mode (e.g., a viewfinder mode or a local 3D rendering mode), viewfinder logic 118 and/or local 3D rendering logic 120 of local intraoral scan application 115 may additionally perform one or more additional operations.

In some embodiments, viewfinder logic 118 determines a frame rate to output images (e.g., 2D color images) to a display, such as display 156, display 190, a touch screen integrated into scanner 150, and so on. The determined frame rate may be a lower frame rate than a frame rate at which the images were generated by the scanner 150. By reducing the frame rate, viewfinder logic 118 may control or affect a speed at which a doctor performs intraoral scanning. In some embodiments, viewfinder logic 118 determines a frame rate for presentation of images dynamically based on one or more criteria. For example, viewfinder logic 118 may determine one or more properties of a scanned surface by analyzing received images and/or intraoral scans, and may set a refresh rate based on the one or more properties. For example, if an upper threshold amount of shadows, grooves, tooth crowding, etc. are detected, or a preparation tooth, a back molar, etc. are detected, based on analysis of the images and/or intraoral scans, viewfinder logic 118 may determine that the refresh rate should be reduced (e.g., due to a difficulty of scanning such areas and/or an increased amount of data generally necessary for representing such areas). On the other hand, if less than the threshold amount of shadows, grooves, tooth crowding, etc. are detected and/or a preparation tooth and/or back molar are not detected, then a higher refresh rate may be selected.

In some embodiments, viewfinder logic 118 analyzes at least some of the received images and/or intraoral scans to determine a difficulty level associated with scanning a current region of a patient's dental arch. This may include applying one or more image processing algorithms to the images and/or intraoral scans and/or inputting the images and/or intraoral scans into a trained machine learning model that outputs a difficulty level rating. In some embodiments, the trained machine learning model is executed on additional processing device 135, which may be hardware optimized for execution of trained machine learning models 138.

In some embodiments, viewfinder logic 118 applies a dynamic frame rate, which is adjusted periodically or continuously based on one or more frame rate criteria. In some embodiments, viewfinder logic 118 applies a static frame rate, which may be a fixed frame rate that is lower than a frame rate at which images are generated. In some embodiments, a user may select between a fixed frame rate and a dynamic frame rate via a user interface of the local intraoral scan application 115.

A user may provide a command or request to enter a local 3D rendering mode. In one example, the scanner 150 receives a user input to enter the local 3D rendering mode (e.g., via a user interaction with a virtual button associated with the local 3D rendering mode that is displayed on a touch screen of the scanner 150). Responsive to such a request, local intraoral scan application 115 may invoke local 3D rendering logic to enable the local 3D rendering mode.

While the local 3D rendering mode is inactive, local intraoral scan application 115 may not generate 3D surfaces based on received intraoral scans in order to reduce computational operations. This may be sufficient in most instances. However, for some use cases a particular region of a dental arch may have increased complexity and/or increased need for high definition. For example, there is generally a need for higher definition for a preparation tooth, and in particular for a margin line of a preparation tooth. Accordingly, for such use cases a doctor may invoke the local 3D rendering mode.

Once the local 3D rendering mode is enabled, local 3D rendering logic 120 begins registering intraoral scans together, stitching the intraoral scans together, and building a 3D surface based on the stitched together intraoral scans. Processing device 108 may have sufficient resources to build a 3D surface for a small region or portion of a patient's dental arch, such as for a single tooth (e.g., a preparation tooth) or a few teeth. In embodiments, intraoral scans that are received after entering the local 3D rendering mode are used to build the 3D surface, and intraoral scans received before entering the local 3D rending mode are not used to build the 3D surface. As the 3D surface is generated, it may be output to a display, such as display 156, display 190, and/or a display integrated into intraoral scanner 150.

To generate the 3D surface, intraoral scan application 115 may register and "stitch" or merge together the intraoral scans generated from the intraoral scan session in real time or near-real time as the scanning is performed. In one embodiment, performing registration includes capturing 3D data of various points of a surface in multiple scans (views from a camera), and registering the scans by computing transformations between the scans. The 3D data may be projected into a 3D space for the transformations and stitching. The scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans and/or reduced or cropped scans. Registration algorithms are carried out to register two or more adjacent intraoral scans and/or to register an intraoral scan with an already generated 3D surface, which essentially involves determination of the transformations which align one scan with the other scan and/or with the 3D surface. Registration may involve identifying multiple points in each scan (e.g., point clouds) of an scan pair (or of a scan and the 3D model), surface fitting to the points, and using local searches around points to match points of the two scan (or of the scan and the 3D surface). For example, local 3D rendering logic 120 may match points of one scan with the closest points interpolated on the surface of another image, and iteratively minimize the distance between matched points. Other registration techniques may also be used. Local 3D rendering logic 120 may repeat registration and stitching for all scans of a sequence of intraoral scans and update the 3D surface as the scans are received.

In one embodiment, the scanner 150 is used as an input device to control the view of the 3D surface of a dental site. Embodiments of the present invention enable a user to perform operations (such as to control or navigate a user interface of intraoral scan application 115 and/or to manipulate medical images or a representation generated from medical images) while still engaged with a patient. Scanner 150 may include one or more buttons, one or more touch sensitive inputs (e.g., touch pads and/or touchscreens) and/or one or more inertial measurement devices (e.g., accelerometers and/or gyroscopes) that may be used to navigate the user interface of the local intraoral scan application 115 and/or manipulate a generated 3D surface.

A user (e.g., a practitioner) may navigate through scanning segments (e.g., an upper dental arch segment, a lower dental arch segment, a bite segment, and optionally a separate segment for each preparation tooth) via a user interface (UI) of the intraoral scan application 115 by various input devices, such as a cursor control device (e.g., a mouse), a remote control (e.g., of a smart TV), a touch input device (e.g., touchscreen) of a scanner 150, etc. In embodiments, a scanner 150 may allow the user to easily navigate or control the user interface of the intraoral scan application 115 using the touch input and/or buttons of the scanner 150. For example, the user may utilize a combination of buttons and various touch gestures on the touch sensor of the scanner 150 to navigate the intraoral scan application 115. In some embodiments, intraoral scanner 150 includes a touchscreen that outputs one or more virtual buttons. A user may interact with the one or more virtual buttons (e.g., by pressing a virtual button) to send a control signal to the intraoral scan application 115. Which virtual buttons are displayed on the intraoral scanner's 150 touchscreen may depend on a current mode of the intraoral scan application 115.

In some embodiments, the user interface for the local intraoral scan application 115 is a simplified user interface that is presented at least in part via a display (e.g., touch screen) integrated into scanner 150. For example, a touch screen of scanner 150 may present virtual buttons providing options for selecting between a dynamic and static refresh rate, for enabling and disabling a local 3D rendering mode, for switching between segments to be scanned, and so on.

Navigation or control of the user interface of the intraoral scan application 115 may be performed via user input. The user input may be performed through various devices, such as a touch input device (e.g., a touchscreen), keyboard, mouse, or other similar control devices of one or more device wirelessly connected to local device 105. User input may also be provided via scanner 150 in embodiments, such as via a touchpad and/or touchscreen of the intraoral scanner 150. Navigation of the user interface may involve, for example, navigating between various modules or modes, navigating between various segments, controlling the viewing of the 3D rendering, or any other user interface navigation. A touch sensitive scanner (e.g., which may include a touchscreen) allows the user to navigate or control the user interface without continuously disengaging from the patient.

In one embodiment, intraoral scan application 115 includes a touch input module (not shown) that receives and interprets touch input data from scanner 150. Scanner 150 may receive different types of touch input such as hold gestures, swipe gestures, tap gestures, circular gestures, and so on. Additionally, or alternatively, a touchscreen of the intraoral scanner 150 may display multiple different virtual buttons, and user interaction with each of the virtual buttons may trigger a different action in local intraoral scan application 115. The touch input module may determine a type of touch gesture that a user performed based on the received touch input and/or what virtual button was pressed based on a detected finger. The touch input module may then initiate functions or operations of the user interface (or intraoral scan application generally) responsive to the determined touch gesture. The functions or operations that are initiated may depend both on the current mode of the intraoral scan application 115 and the determined touch gesture and/or pressed virtual button. Accordingly, the same touch gesture or finger interaction with a same region of the touchscreen may cause a first function to be performed in a first mode of the intraoral scan application and may cause a second function to be performed in a second mode. Specific modes of operation and touch gestures and/or virtual buttons that initiate operations or functions for those modes are discussed in greater detail below.

In one embodiment, local device 105 executing local intraoral scan application 115 receives a touch input from a touch sensor (e.g., a touchpad or touchscreen) of scanner 150 (e.g., which may include a press of a virtual button on a touchscreen) and/or a button press from a button of scanner 150 during an intraoral scan session. In one embodiment, local intraoral scan application 115 determines whether the touch input is a hold gesture or a swipe gesture. The computing device may then perform a first function or operation to control a user interface of the intraoral scan application if the touch input is a hold gesture (or a particular button of virtual button is depressed) and a second function or operation to control the user interface of the intraoral scan application if the touch input is a swipe gesture (or another button or virtual button is depressed). Examples of functions that may be performed include activating a gyroscope in the intraoral scanner 150, using data from the gyroscope to control an orientation of a virtual 3D surface (e.g., if a hold gesture is detected) and proceeding to next or previous scan segments (e.g., if a swipe gesture is detected). The functions or operations performed responsive to the hold or swipe gestures and/or responsive to a user pressing a virtual button of a touchscreen on the intraoral scanner 150 may be functions that traditionally are performed responsive to a user using a keyboard, mouse and/or touchscreen of a computer. Results of the inputs from the scanner 150 (e.g., button pushes, virtual button pushes, swipe gestures, hold gestures, movement of the scanner 150, etc.) may cause one or more menus or options of the intraoral scan application 115 to be navigated or transitioned between, and/or an updated menu or options to be output to a display 156, 190 associated with the intraoral scanner 150 and/or to a touchscreen of the intraoral scanner 150. In some embodiments, pressing a particular button or buttons (including one or more virtual buttons of a touchscreen) or performing a hold gesture of a touch sensitive input causes local intraoral scan application 115 to output a navigation overlay to a display 156, 190. While and/or after the button(s) and/or virtual buttons are pushed and/or during the hold gesture of the touch sensitive input, a user may move the scanner 150 and motion of the scanner may be used as an input to navigate the navigation overlay. For example, the scanner 150 may be moved left to select a first menu option (e.g., switch to previous scan segment), right to select a second menu option (e.g., switch to next scan segment), up to select a third menu option or down to select a fourth menu option. The movement of the scanner may register as an input that causes a user interface of the intraoral scan application 115 to be updated, and the updated user interface may be output to the display 156, 190 associated with scanner 150.

By providing touch sensors, touchscreens and/or buttons in the intraoral scanner 150 and an intraoral scan application 115 that can respond to touch input from such touch sensors, that can respond to input from touchscreens (e.g., presses of virtual buttons displayed on a touchscreen) and/or that can respond to use of the buttons, embodiments improve the efficiency of performing intraoral scans. Additionally, display 156 may not include an input device for controlling intraoral scan application 115. However, scanner 150 may function as such an input device for controlling intraoral scan application 115. For example, if the intraoral scan application 115 is outputting image data to display 156, then a user of scanner 150 may press a physical button, press a virtual button of a touchscreen on the intraoral scanner 150 and/or use a hold gesture on a touch input of the scanner 150 to activate a view mode. During the view mode, the user may move the scanner and/or interface with the touchscreen or touch pad on the intraoral scanner 150 to rotate a view of a 3D surface or 3D model of a dental site. The user may release the button, virtual button or hold gesture to resume a scanning mode and continue generating intraoral scans. Alternatively, the user may press a different virtual button to resume the scanning mode and continue generating intraoral scans.

When a scan session is complete (e.g., all scans for an intraoral site or dental site have been captured), local intraoral scan application 115 may send the intraoral scan data (e.g., including at a minimum intraoral scans) to remote server computing device 106 for processing by remote intraoral scan application 116. Remote intraoral scan application 116 may include a model generator 122 that may process the intraoral scan data to generate one or more virtual 3D model of a patient's dental arch or dental arches. Model generator 122 may generate a virtual 3D model (also referred to as a digital 3D model) of one or more scanned dental sites. The virtual 3D model includes a 3D surface of the one more scanned dental sites. To generate the virtual 3D model, model generator 122 may register and "stitch" or merge together the intraoral scans generated from the intraoral scan session. In one embodiment, registration is performed for adjacent and/or overlapping intraoral scans (e.g., each successive frame of an intraoral video). In one embodiment, registration is performed using blended scans and/or reduced or cropped scans. Registration algorithms may be carried out to register two or more adjacent intraoral scans and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, model generator 122 may match points of one scan with the closest points interpolated on the surface of another scan, and iteratively minimize the distance between matched points. Other registration techniques may also be used. The registration and stitching that are performed to generate the 3D model may be more accurate than the registration and stitching that are performed to generate the 3D surface that is shown in real time or near-real time during the scanning process.

Model generator 122 may repeat registration for all scans of a sequence of intraoral scans to obtain transformations for each scan, to register each scan with the previous one and/or with a common reference frame (e.g., with the 3D model). Model generator 122 may integrate all scans (or all scans associated with a segment) into a single virtual 3D model by applying the appropriate determined transformations to each of the scans. Each transformation may include rotations about one to three axes and translations within one to three planes. In some embodiments, a first model of an upper dental arch and a second model of a lower dental arch are generated.

A user (e.g., a dentist) may access and view the virtual 3D model(s) by accessing a user interface 124 of remote intraoral scan application 116 from a client computing device 195. The client computing device 195 may be any computing device, such as a tablet computer, a desktop computer, a mobile phone, a laptop, a notebook computer, and so on.

User interface 124 of remote intraoral scan application 116 may generate a view of the 3D model and output the view to client computing device 195 for display of the 3D model to a user (e.g., a doctor) via a display of the client computing device 195. A doctor may then interface with the client computing device 195 to generate commands to change the view of the 3D model (e.g., by zooming in or out, panning, rotating, etc.). The client computing device 195 may send the command to remote intraoral scan application 116, which may change the view of the 3D model, and then send the updated view to the client computing device 195. In this manner, the 3D model can be checked visually by the doctor. The doctor can virtually manipulate the 3D model via the user interface of the client computing device 195 with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

In one embodiment, remote intraoral scan application 116 includes a treatment planner 123 configured to perform treatment planning for orthodontic treatment and/or prosthodontic treatment. Treatment planner 123 may additionally perform dental diagnostics and/or prognostics. Via the user interface 124, a practitioner may view one or more of the upper dental arch, the lower dental arch, a particular preparation tooth and/or the patient bite, each of which may be considered a separate scan segment or mode. The treatment planner 123 in embodiments generates an orthodontic treatment plan, including a 3D model for a final tooth arrangement and 3D models for one or more intermediate tooth arrangements. Treatment planner 123 may additionally or alternatively perform diagnostics of a patient's oral cavity and/or provide a prognosis of one or more dental conditions and/or suggested treatments for the one or more dental conditions. The treatment planner 123 may further perform one or multiple different analyses of the patient's dental arches and/or bite. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. Once the analyses are complete, a dental diagnostics summary and/or detailed dental diagnostics information optionally including prognosis and/or treatment options may be presented to a client computing device 195. A doctor may control the treatment planner 123 and navigate menus and options of the treatment planner using the client computing device 195.

In an example, a patient who wishes to straighten their teeth may opt for Invisalign® treatment. Invisalign is a process that creates a custom made series of clear aligners specifically for the patient. The clear aligners are worn over the patient's teeth and gradually shift the patient's teeth. A new set of aligners may be worn after a specified period of time (e.g., two weeks) until treatment is complete.

The patient may visit a dental practitioner or orthodontist to begin Invisalign treatment. The dental practitioner may utilize intraoral scanning system 100 to scan the patient's teeth. No 3D surfaces may be generated or presented to the dental practitioner during the intraoral scanning. In some embodiments, the only visual feedback that the dental practitioner receives during scanning is 2D color images generated by the intraoral scanner at a first frame rate and displayed at a second frame rate (where only a subset of the 2D color images are displayed). The dental practitioner may use scanner 150 to capture the patient's teeth segments (e.g., upper arch, lower arch, bite segments) in one or more sets of intraoral scans.

The local device 105 stores the intraoral scans generated from the intraoral scanning session. Once scanning is complete, the local device 105 sends the intraoral scans to remove server computing device for processing. Alternatively, local device 105 may send the intraoral scans (and optionally other intraoral scan data such as 2D color images, 2D NIRI images, etc.) to the remote server computing device before scanning is complete (e.g., during intraoral scanning). The remote intraoral scan application 116 executing on the remote computing device 106 may register and stitch together the intraoral scans to create a 3D rendering or model of the scanned segments. The dental practitioner may then access the 3D rendering or model(s) from client computing device 195.

Treatment planner 123 of remote intraoral scan application 116 may determine a final tooth arrangement and one or more intermediate tooth arrangements for a patient. A treatment plan may be generated to provide a progression of treatment stages from the patient's initial tooth arrangement to the target final tooth arrangement, where a separate 3D model is associated with each treatment stage.

Once an adequate set of 3D models is generated, the 3D models may be saved to the patient profile. The dental practitioner may then navigate to a delivery mode to electronically send the completed patient profile to a processing center. The processing center may then generate the custom made series of clear aligners for the patient and deliver the clear aligners to the dental practitioner. The patient would then return to the dental practitioner to receive the first set of clear aligners and verify the clear aligners properly fit onto the patient's teeth.

Figure 1B:
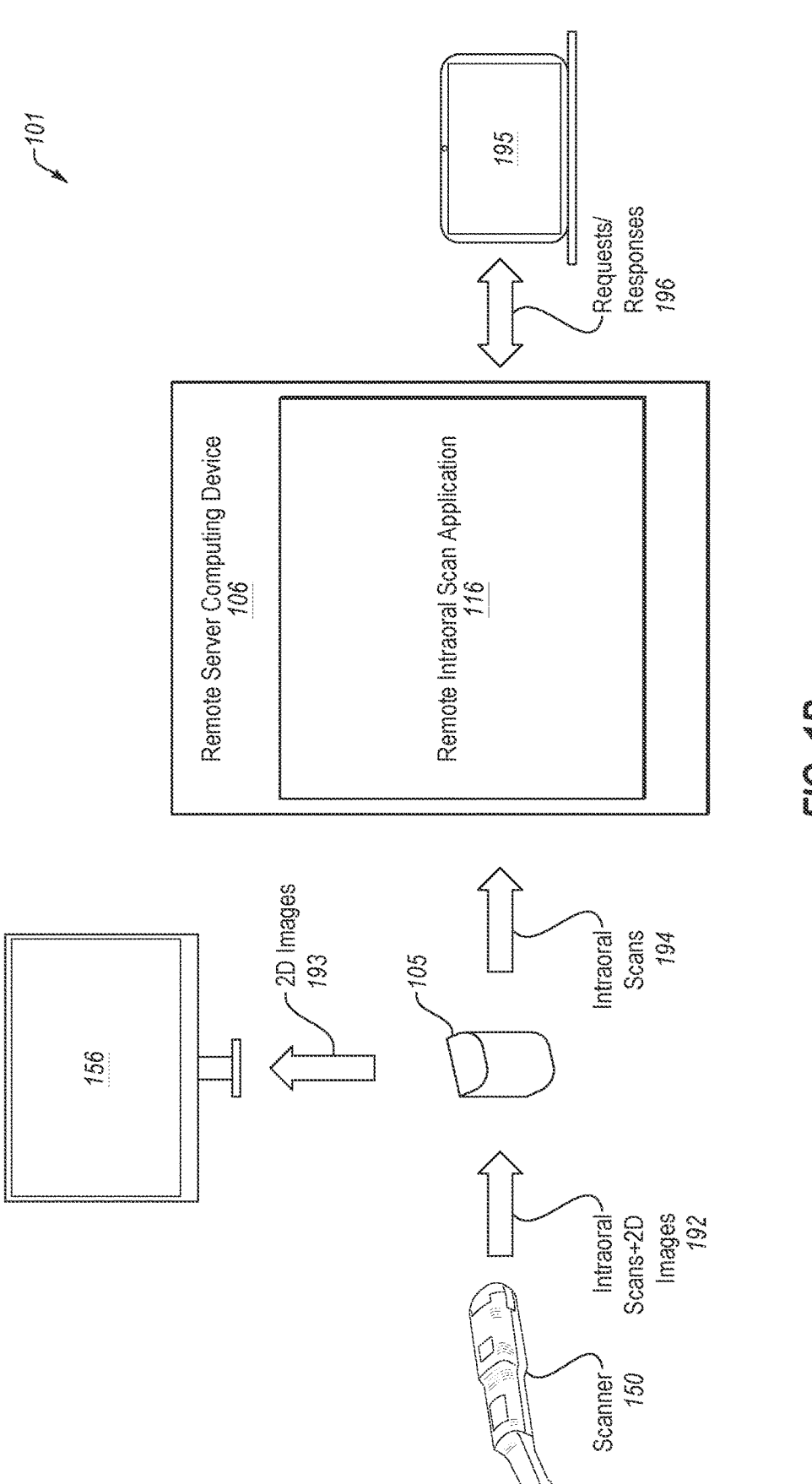
FIG. 1B illustrates message flow for a minimalistic intraoral scanning system, in accordance with an embodiment.

FIG. 1B illustrates message flow 101 for a minimalistic intraoral scanning system, in accordance with an embodiment. The minimalistic intraoral scanning system includes scanner 150 and local device (e.g., cradle) 105. Associated with the minimalistic intraoral scanning system is an optional display 156, which may be at a location of the scanner 150 and local device 105. The intraoral scanning system may correspond to intraoral scanning system 100 of FIG. 1A in embodiments.

Each local device 105 may be a charging station and/or cradle used to hold and charge scanner 150. In some embodiments, local device 105 include a wireless charger that wirelessly charges a scanner 150 (e.g., that includes one or more rechargeable batteries) having wireless charging capability that is placed in or on the cradle. For example, a cradle may include a primary induction coil and a scanner 150 may include a secondary induction coil. The primary induction coil of the cradle may induce a current in the secondary induction coil of the scanner 150 to charge the scanner 150 via resonant inductive coupling. In such embodiments, the scanner 150 may not include exposed charging pins. Additionally, scanner 150 and cradle may support other types of wireless charging technologies, such as radio charging, and resonance charging.

In some embodiments, the cradle includes pins that engage with exposed charging pins of a scanner 150 (e.g., that includes one or more rechargeable batteries) when the scanner 150 is placed in the cradle. The cradle may then perform wired charging of the scanner 150 via contact between the pins of the cradle and the exposed charging pins of the scanner 150.

When scanner 150 is inserted into a cradle, a physical connection between the scanner 150 and cradle may be established, and the cradle may charge a battery of scanner 150 via the physical connection. Alternatively, wireless charging may be performed to charge a battery of scanner 150.

In FIG. 1B, arrows show the direction of information flow, according to at least one embodiment. As shown, scanner 150 sends intraoral scan data (e.g., intraoral scans and 2D images) 192 to local device (e.g., cradle) 105. The 2D images may be generated by scanner 150 at a first frame rate. Local device 105 then stores at least a portion of the intraoral scan data (e.g., intraoral scans and optionally 2D images) in local storage. Local device 105 additionally outputs the 2D images to display 156 at a second frame rate that is lower than the first frame rate.

As scanning is performed and/or once scanning is complete, local device 105 sends at least intraoral scans 194 to remote server computing device 106. In embodiments, local device 105 sends all collected and stored intraoral scan data to remote server computing device 106 (e.g., which may include intraoral scans, color 2D images, NIRI images, etc.). As discussed with reference to FIG. 1A, a remote intraoral scan application 116 running on remote server computing device 106 generates one or more 3D models based on the intraoral scans (and optionally 2D color and/or NIRI images). A user may access, view and modify the 3D models by sending requests 196 from and receiving responses 196 at a client computing device 195.

Figure 2:
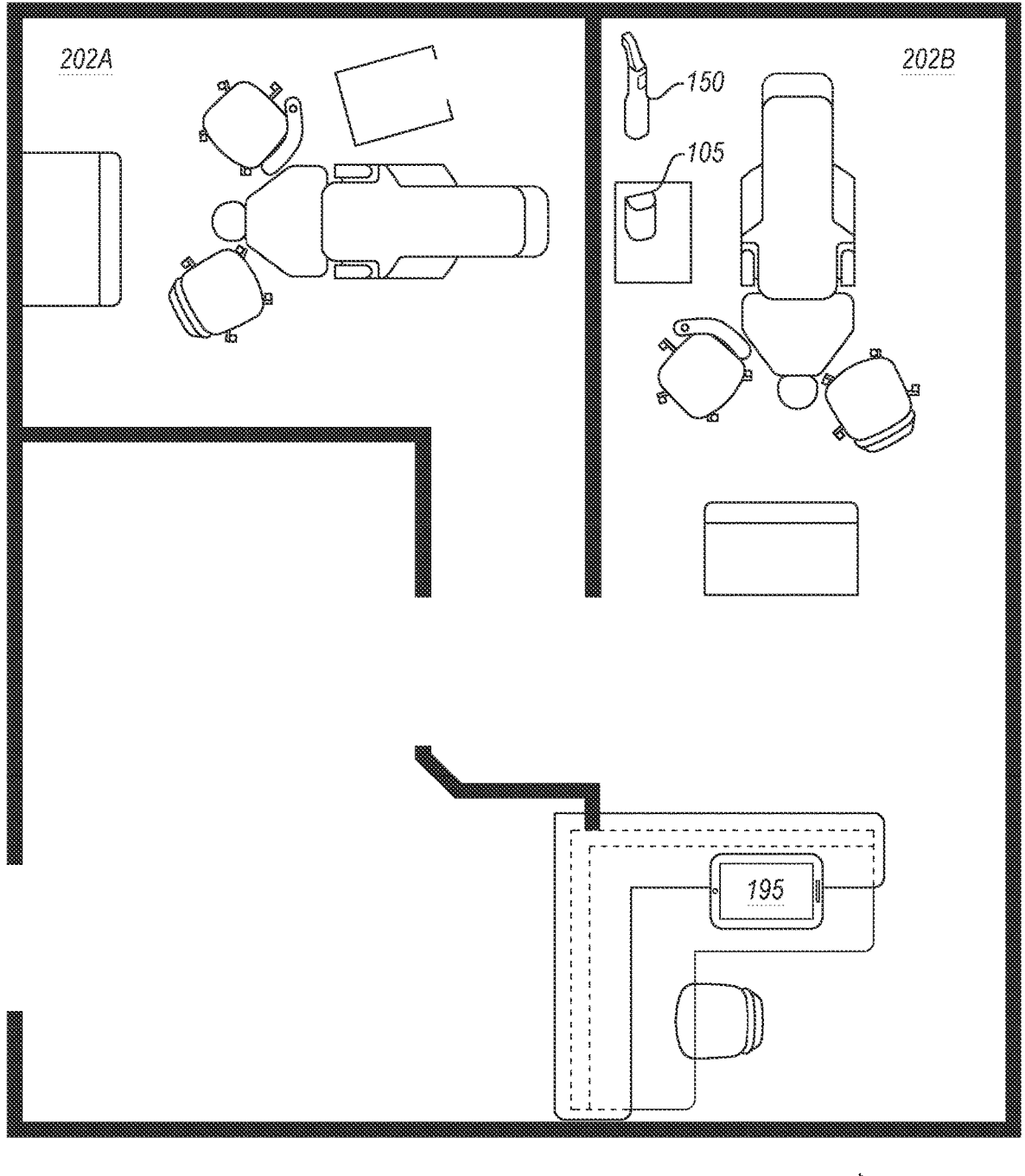
FIG. 2 illustrates an example dentist office that includes a minimalistic intraoral scanning system, in accordance with an embodiment.

FIG. 2 illustrates an example dentist office 200 that includes an intraoral scanning system, in accordance with an embodiment. The intraoral scanning system may correspond to intraoral scanning system 100 in embodiments. As shown, the dentist office 200 includes a receptionist area and multiple rooms 202A, 202B. Rooms 202A-202B are treatment rooms that each include a dental chair. The rooms may or may not include displays. Only a single treatment room 202B includes an intraoral scanning system, which includes an intraoral scanner 150 and a local device (e.g., cradle or charging station) 105. The dentist office may be a basic dentist office that lacks expensive equipment such as large displays, desktop computers, and so on. A dentist may use the intraoral scanning system to generate intraoral scans, which may be sent to a remote server and processed thereon to generate one or more 3D models of the patient's dental arches. The dentist may include client computing device 195

(e.g., which may be a tablet computer, laptop computer, etc.), and may view the generated 3D model(s) therefrom after scanning is complete.

FIGS. 3A-6 illustrate methods related to intraoral scanning of dental sites using a simplified intraoral scanning system, according to embodiments. Operations of the methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by an intraoral scanning system that includes an intraoral scanner and a local device (e.g., a cradle and/or charging station for the intraoral scanner).

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

Figure 3A:
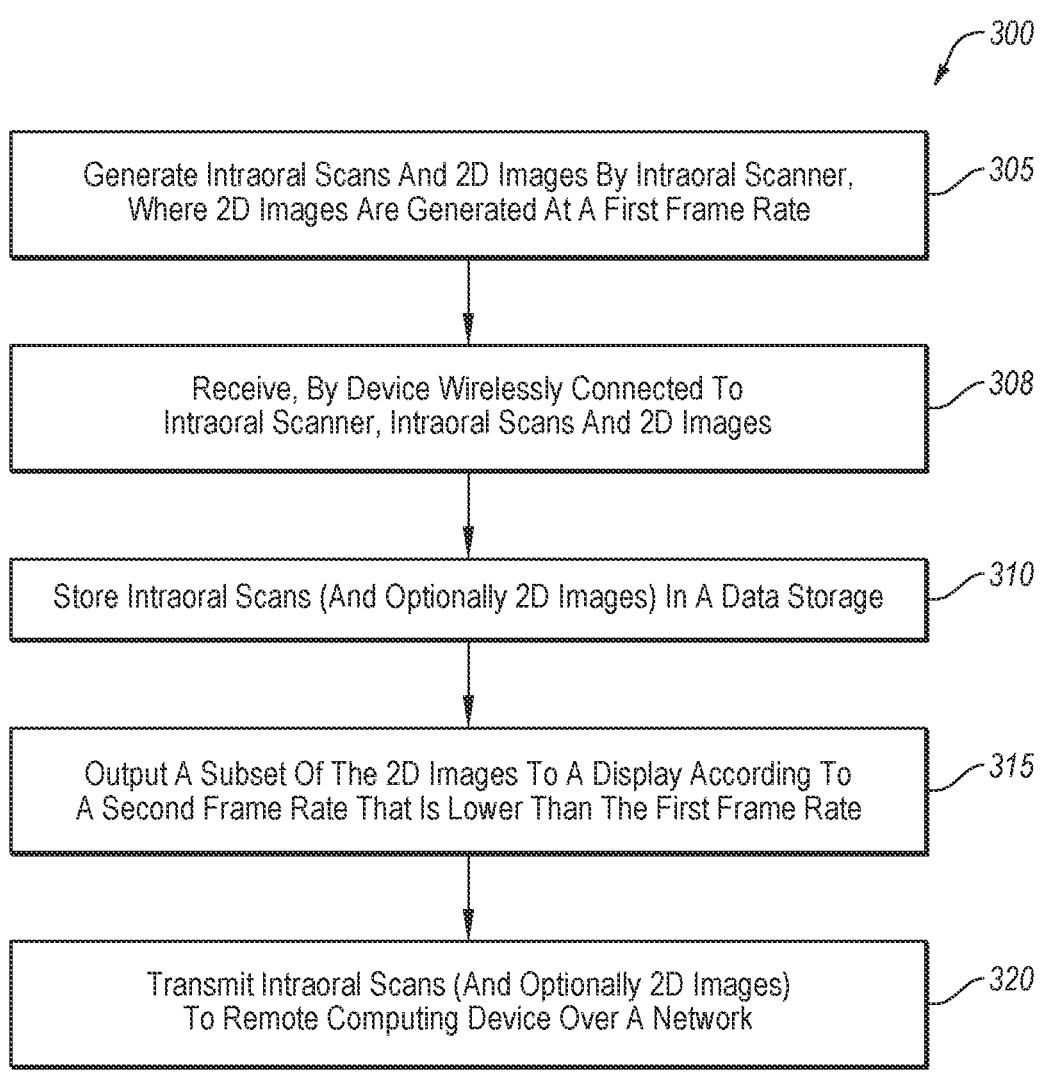
FIG. 3A illustrates a flow diagram for a method of processing intraoral scans using an intraoral scanning system, in accordance with an embodiment.

FIG. 3A illustrates a flow diagram for a method 300 of processing intraoral scans using an intraoral scanning system (e.g., a simplified or minimalistic intraoral scanning system), in accordance with an embodiment. At operation 305 of method 300, an intraoral scanner generates intraoral scan data of a patient's oral cavity (including intraoral scans and 2D images). The 2D images are generated at a first frame rate.

At block 308, the intraoral scanner sends, and processing logic of a local device (e.g., a cradle or charging station for the intraoral scanner) receives, the intraoral scan data. At block 308, the processing logic stores the intraoral scans, and optionally other intraoral scan data (e.g., the 2D images) in a local data storage. At block 315, processing logic outputs a subset of the 2D images to a display according to a second frame rate that is lower than the first frame rate. The display may be, for example, a monitor or television at a location where intraoral scanning is being performed. The display may additionally or alternatively include a small display of the local device and/or a display of the intraoral scanner itself.

At block 320, the processing logic transmits the intraoral scans (and optionally other intraoral scan data such as the 2D images) to a remote computing device over a network for processing.

FIG. 3B illustrates a flow diagram for a method 350 of processing intraoral scans using an intraoral scanning system, in accordance with an embodiment. At operation 355 of method 350, processing logic of a cradle or charging station for an intraoral scanner receives, from the intraoral scanner during intraoral scanning, intraoral scan data including at least intraoral scans and 2D images generated by the intraoral scanner. The 2D images may be generated at a first frame rate.

At block 360, processing logic stores the intraoral scans, and optionally other intraoral scan data (e.g., the 2D images), in a local data storage.

At block 365, processing logic determines a frame rate to use for presenting the 2D images. In one embodiment, processing logic determines properties of a scanned surface (e.g., from the intraoral scans and/or 2D images) and/or a difficulty of scanning the intraoral surface. In some embodiments, this can include inputting the intraoral scans and/or 2D images into a trained machine learning model or image processing algorithm. The trained machine learning model and/or image processing algorithm may process the input intraoral scan data and output one or more determined properties of the surface (e.g., an indication that the surface includes tooth crowding, that image clarity is low, etc.) and/or a difficulty level associated with a difficulty of scanning the intraoral surface. At block 375, processing logic may determine a frame rate for presenting the 2D images to a display based on the determined properties and/or the determined difficulty level determined at block 370. For example, if the difficulty level is high, then the frame rate may be reduced to slow down a speed at which a user moves the intraoral scanner. In another example, if the difficulty is low, then the frame rate may be increased to increase the speed at which the user moves the intraoral scanner during intraoral scanning.

At block 380, processing logic outputs a subset of the 2D images to a display according to the determined frame rate. In embodiments, the determined frame rate is below the first frame rate at which the 2D images are generated. In some instances, the determined frame rate may be equal to the first frame rate at which the 2D images are generated (e.g., for areas with a very low level of scanning difficulty).

At block 385, processing logic determines whether scanning is complete. If scanning is not complete, the method returns to block 355 and additional intraoral scan data is received. When the method eventually proceeds again to block 365, a new frame rate for presenting 2D images may again be determined. The new frame rate may be the same as the previously determined frame rate or may be different from the previously determined frame rate. Accordingly, the frame rate may be adjusted dynamically based on conditions of the dental sites being scanned.

If at block 385 a determination is made that scanning is complete, the method proceeds to block 390. At block 390, the processing logic transmits the intraoral scans (and optionally other intraoral scan data such as the 2D images) to a remote computing device over a network for processing. In embodiments, processing logic may also transmit intraoral scans and/or other intraoral scan data to the remote computing device before intraoral scanning is complete (e.g., as intraoral scan data is generated) in some embodiments.

FIG. 4 illustrates a flow diagram for a method 400 of processing intraoral scans using an intraoral scanning system, in accordance with an embodiment. At operation 402 of method 400, an intraoral scanner starts an intraoral scan. At operation 405, the intraoral scanner generates intraoral scan data, which may include intraoral scans, color images and/or other images generated under specific lighting conditions (e.g., under infrared or near-infrared light). At operation 410, the intraoral scanner compresses the intraoral scan data. In one embodiment, video compression techniques are used to compress the intraoral scan data. Compressing the intraoral scan data may include compressing intraoral scans, compressing color images and/or compressing near-infrared images. Additionally, or alternatively, the intraoral scanner may perform reduction on the intraoral scan data (e.g., on intraoral scans) by identifying areas of interest and cropping intraoral scans to include only the areas of interest. At operation 415, the intraoral scanner wirelessly transmits the compressed and/or reduced intraoral scan data to a local server computing device.

At operation 420, the local device (e.g., cradle and/or charging station for the intraoral scanner) receives the compressed and/or reduced intraoral scan data. At block 425, the local device stores at least some of the compressed intraoral scan data.

At operation 430, the local server computing device decompresses at least a subset of the compressed intraoral scan data (if it was compressed). For example, the local server computing device may decompress just a subset of the compressed color images. The subset to decompress may be selected based on a determined frame rate at which the images are to be output to a display, which may be determined as described above with reference to methods 300 and 350.

At operation 435, the local device determines a target device (e.g., display or computing device) to output the color images to. At operation 440, the local device outputs the subset of decompressed color images to the determined display at the determined refresh rate or frame rate, which may be lower than a refresh rate or frame rate at which the images were generated.

At operation 445, the local device determines whether the scan is complete. The scan may be determined to be complete responsive to a command from the intraoral scanner to exit a scanning mode, for example. If the scan is not complete, the method returns to operation 405 and scanner generates additional intraoral scan data. If the scan is complete, the method continues to operation 450, and the scan is stopped. At any time during and/or after scanning the stored compressed intraoral scan data may be sent to a remote computing device for processing (e.g., to generate a 3D model, develop a treatment plan, etc.).

Figure 5:
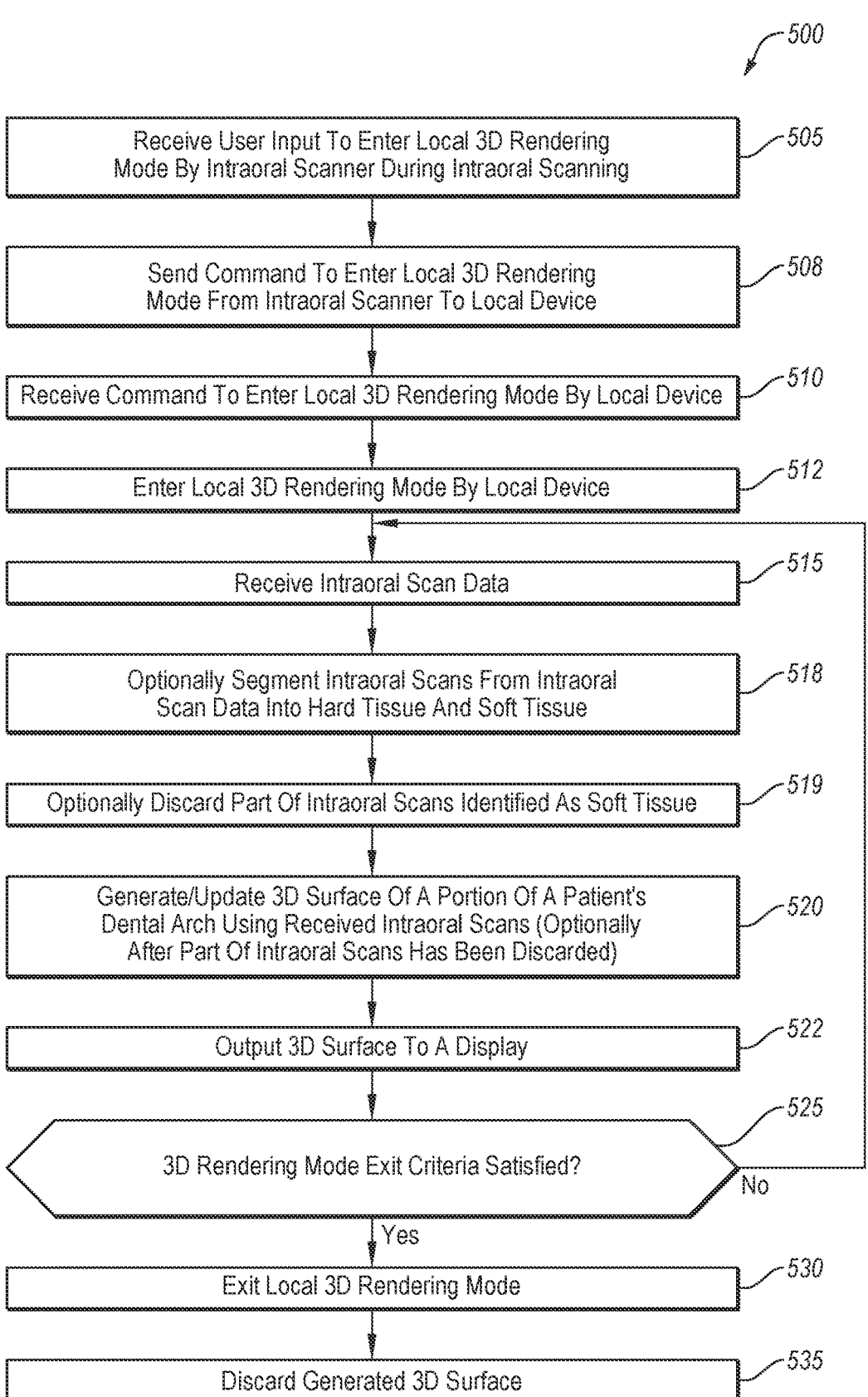
FIG. 5 illustrates a flow diagram for a method of executing a local 3D rendering mode for an intraoral scanning system, in accordance with an embodiment.

FIG. 5 illustrates a flow diagram for a method 500 of executing a local 3D rending mode for an intraoral scanning system, in accordance with an embodiment. At operation 505 of method 500, an intraoral scanner receives a user input to enter a local 3D rendering mode during intraoral scanning. The user input may be received, for example, based on a user pressing a touch sensor, a physical button and/or a virtual button presented on a touchscreen of the intraoral scanner.

At block 508, the intraoral scanner sends a command to enter the local 3D rendering mode to a local device associated with the intraoral scanner. In embodiments, the local device is a cradle and/or charging station for the intraoral scanner that includes an embedded system, a system on a chip (SoC), and/or other low cost computing device that is integrated into the local device (e.g., into the cradle/charging station). At block 510, the local device receives the command to enter the local 3D rendering mode, and at block 512 the local device enters the local 3D rendering mode.

At block 515, the local device receives intraoral scan data. The intraoral scan data may include, at a minimum, intraoral scans and 2D images in some embodiments. At block 518, the local device optionally segments intraoral scans from the intraoral scan data into hard tissue and soft tissue. Such segmentation may be performed by inputting the intraoral scans into a trained machine learning model (e.g., a convolutional neural network (CNN)), which may output a probability map indicating, for each point or pixel of an intraoral scan, whether that point or pixel is classified as soft tissue or hard tissue. The trained machine learning model or another trained machine learning model may also process the intraoral scans to segment the intraoral scans into regions classified as moving tissue and regions not classified as moving tissue. The trained machine learning model or another trained machine learning model may also process the intraoral scans to segment the intraoral scans into regions classified as excess tissue and regions not classified as excess tissue.

At block 519, processing logic of the local device may discard, filter out, or otherwise ignore parts of the intraoral scans that have been classified as soft tissue, as moving tissue and/or as excess tissue. Remaining parts of the intraoral scans may be those parts that were classified as hard tissue. At block 520, processing logic may generate a 3D surface of a portion of a patient's dental arch using the received intraoral scans. If the intraoral scans were filtered (e.g., some portion of them was removed or ignored), then those remaining portions (e.g., the parts classified as hard tissue) may be used to generate the 3D surface without using the remainder of the intraoral scans that were not classified as hard tissue. This may reduce a computational load associated with generating the 3D surface. In embodiments, the generated 3D surface may be a relatively small 3D surface, such as for a single tooth or a few teeth, as opposed to a conventional larger 3D surface generated for a full dental arch as is typically generated during intraoral scanning. If a 3D model was previously generated from previous intraoral scans, then the current intraoral scans may be used to update the 3D surface. At block 522, the 3D surface may be output to a display, such as a display on an intraoral scanner, a monitor, a TV, or a display integrated into the local device.

At block 525, processing logic determines whether a 3D rendering mode exit criterion has been satisfied. The local device may be a resource constrained device with minimal processing power. Accordingly, in some embodiments the local device may only have sufficient processing resources to generate a small 3D surface. Once those processing resources are fully utilized, it may be prudent to exit the local 3D rendering mode. Accordingly, in embodiments processing logic monitors one more parameters associated with a processing device and/or associated with a generated 3D surface. Such parameters may include, for example, a current amount of processor resources being consumed, a remaining available amount of processor resources, a current amount of memory being consumed, a remaining amount of memory, a size of a generated 3D surface, a number of vertexes or triangles in the 3D surface, and so on. The monitored parameters may be compared against one or more exit criteria, which may include one or more thresholds. If any of the determined parameters satisfies an exit criteria, then the method may proceed to block 530, and the 3D rendering mode may be exited. If none of the determined parameters satisfies an exit criteria, then the method may return to block 515 and processing logic may remain in the local 3D rendering mode and add to an existing 3D surface with additional scans. In an example, if a current processor resource utilization or memory utilization exceeds a threshold, then an exit criterion may be satisfied. In another example, if a remaining processor resources value or a remaining memory value falls below a threshold, an exit criterion may be satisfied. In another example, if a size of the 3D surface exceeds a size threshold or a number of triangles in the 3D surface exceeds a triangle count threshold, then an exit criterion may be satisfied.

In some embodiments, a virtual bounding shape (e.g., bounding box) may be determined around a region in space that is determined based on one or more first intraoral scans that are received after entering the local 3D rendering mode. As intraoral scans are received, they may be assessed to determine which, if any, portions of those intraoral scans fall outside of the bounding shape. Any data falling outside of the bounding shape may be discarded. This may provide an upper threshold for the size and/or complexity of the 3D surface that is generated. In embodiments a user may be prompted to confirm that the 3D surface can be discarded. If the user fails to respond or responds that the 3D surface should not be discarded, the 3D surface may not immediately be discarded. However, no new data may be added to the 3D surface.

Once the local 3D rendering mode has been exited at block 530, the generated 3D surface may be discarded at block 335 to free up memory.

Figure 6:
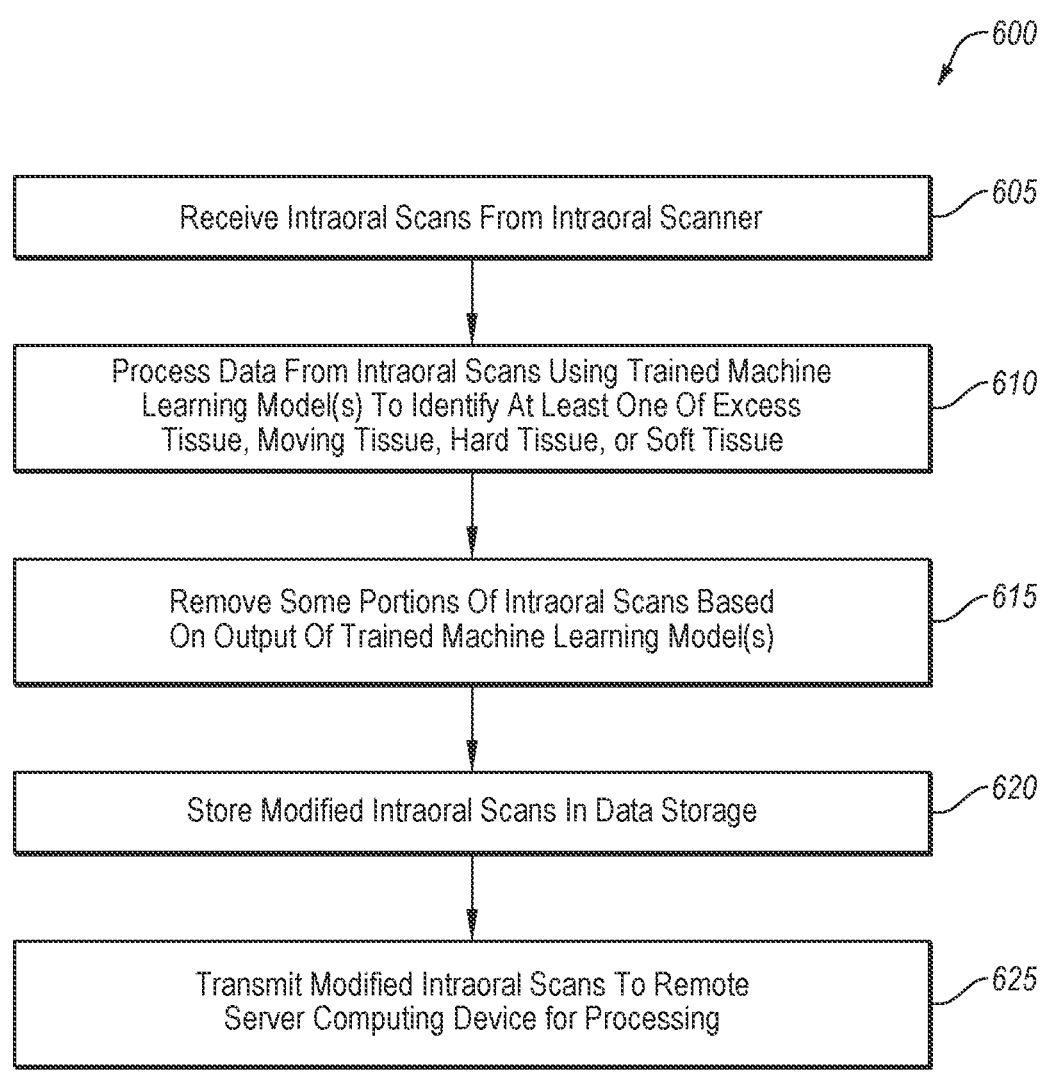
FIG. 6 illustrates a flow diagram for a method of modifying intraoral scans on a minimalistic intraoral scanning system, in accordance with an embodiment.

FIG. 6 illustrates a flow diagram for a method 600 of modifying intraoral scans on a minimalistic intraoral scanning system, in accordance with an embodiment. At operation 605 of method 600, processing logic receives intraoral scan data from an intraoral scanner, wherein the intraoral scan data is of a patient's oral cavity. The intraoral scan data may include 2D or 3D scans, color 2D images, NIRI 2D images, and/or other images.

At operation 610, processing logic processes data from the intraoral scans using one or more trained machine learning models to identify at least one of excess tissue, moving tissue, hard tissue and/or soft tissue. Intraoral scans may be input into the trained machine learning model, which may output a map indicating for each point in the scan whether the point is classified as excess tissue, moving tissue, hard tissue and/or soft tissue.

One type of machine learning model that may be used is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may provide a final output.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and backpropagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

Training of the machine learning model and use of the trained machine learning model (e.g., for an excess material removal algorithm and/or the excess gingiva removal algorithm) may be performed by processing logic executed by a processor of a computing device. For training of the machine learning model, a training dataset containing hundreds, thousands, tens of thousands, hundreds of thousands or more images should be used to form a training dataset. A training dataset may be gathered, where each data item in the training dataset may include an image or scan and an associated label that identifies pixels or points associated with one or more classes such as excess material, moving tissue, soft tissue, hard tissue, and so on.

A machine learning model may be trained using the scans or images with the labeled information. The machine learning model may be trained to classify pixels in images as belonging to one or more classes (e.g., excess tissue, moving tissue, hard tissue, soft tissue, etc.). The result of this training is a function that can segment intraoral scans. In particular, the machine learning model may be trained to generate a probability map, where each point in the probability map corresponds to a pixel or point of an input image or scan and indicates one or more of a first probability that the pixel or point represents a first class, a second probability that the pixel or point represents a second class, a third probability that the pixel or point represents a third class, a fourth probability that the pixel or point represents a fourth class, and so on. In embodiments, the machine learning model may also be trained to identify other dental classes.

During an inference stage (i.e., use of the trained machine learning model), the intraoral scan or scans (and optionally other data) is input into the trained model, which may have been trained as set forth above. The trained machine learning model may output a probability map, where each point in the probability map corresponds to a pixel or point in the scan or image and indicates probabilities that the pixel or point represents one or more dental classes.

At operation 615, processing logic removes some portions of the intraoral scans based on the output of the trained machine learning model(s). For example, points or pixels identified as moving tissue and/or excess tissue may be removed in embodiments. In some embodiments (e.g., where a local 3D rendering mode is active), points or pixels identified as soft tissue may be removed (e.g., temporarily removed so that they are not processed for 3D surface generation).

At operation 620, processing logic may store the modified intraoral scans in a local data storage. At block 625, the modified scans may be transmitted to a remote server computing device for processing. By removing some portion of the intraoral scans (such as portions identified as moving tissue and/or excess tissue), the size of the intraoral scans may be reduced, which in turn reduces amount of storage capacity that is taken up by storage of the intraoral scans and reduces a bandwidth of sending the intraoral scans to the remote server computing device.

Figure 7A:
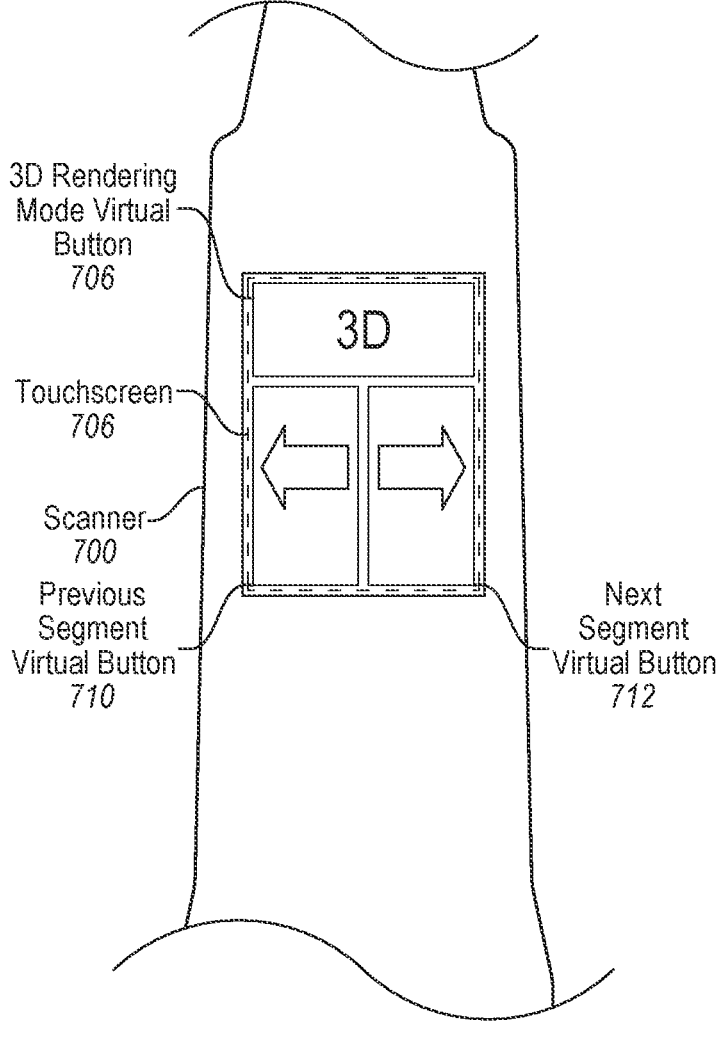
FIGS. 7A-B illustrate example virtual buttons on an intraoral scanner touchscreen, in accordance with embodiments of the present disclosure.

FIG. 7A illustrates an intraoral scanner 700 having a touchscreen 702 displaying a touch interface including a plurality of virtual buttons 706, 710, 712. As shown, each virtual button includes a different graphic, different characters, and so on. A user may use the touchscreen 702 to interface with a local intraoral scan application. In some embodiments, during scanning the touchscreen presents a user interface for controlling intraoral scanning. The touchscreen 702 may present, for example, a 3D rendering mode virtual button 706, which may be used to enter or exit a local 3D rendering mode. The touchscreen 702 may additionally or alternatively present a previous segment virtual button 710 and/or a next segment virtual button 712 for navigating to a next or previous segment of a patient's oral cavity during intraoral scanning (e.g., for transitioning between scanning of a lower dental arch, an upper dental arch, and a patient bite).

The scanning segments may include, for example, an upper dental arch segment, a lower dental arch segment, and a patient bite segment. A user may presently be scanning one of the segments (e.g., upper dental arch segment), and upon completion of that segment may desire to scan a next segment (e.g., a lower dental arch segment). Accordingly, the user may press a next segment virtual button 712 to transition to scanning of a next segment (e.g., lower dental arch segment). Once that segment is complete, the user may again press the next segment button to transition to scanning of a next segment (e.g., patient bite segment). At any time, a user may press a previous segment virtual button 710 to revisit scanning of an already scanned segment. For example, if a user is presently scanning a bite segment, the user may press the previous segment virtual button to transition to scanning of the lower dental arch segment, and may again press the previous segment virtual button to transition to scanning of the upper dental arch segment.

Figure 7B:
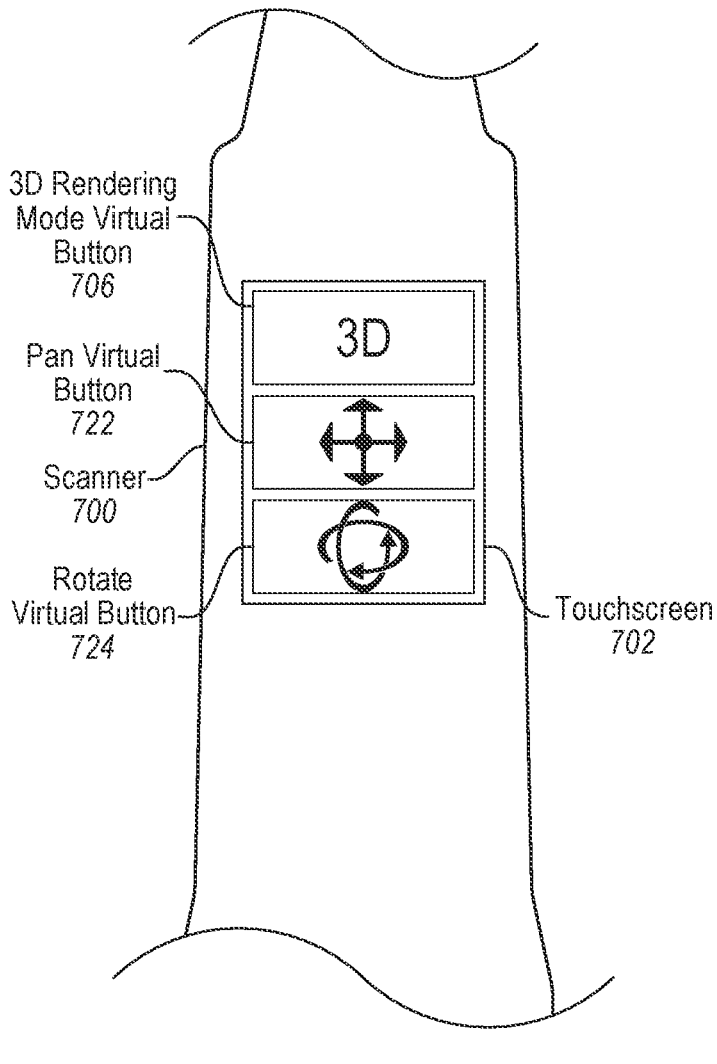

FIG. 7B illustrates an intraoral scanner 700 having a touchscreen 702 displaying an interface associated with a local 3D rendering mode. The displayed interface may be used both for exiting the local 3D rendering mode (e.g., by pressing a 3D rendering mode virtual button 706) and for controlling a view of a 3D surface of a dental site generating while in the local 3D rendering mode, referred to a surface view manipulation. While in the local 3D rendering mode, touchscreen 702 may display, for example, a pan virtual button 722 and/or a rotate virtual button 724. A zoom virtual button (not shown) may also be provided. In one embodiment, a user may press one of the pan virtual button 722, the zoom virtual button or the rotate virtual button 724 to select an appropriate manipulation mode (e.g., a pan mode, zoom mode or rotate mode). In the appropriate mode, further interaction with the touchscreen may cause a particular type of manipulation associated with a current manipulation mode. For example, in the pan mode, dragging a finger across the touchscreen may cause a 3D surface to pan. In the rotate mode, dragging a finger across the touchscreen may cause a 3D surface to rotate. In a zoom mode, dragging a finger across the touchscreen may cause a 3D surface to zoom in or out.

In one embodiment, the user may press on the pan virtual button to pan a view of the 3D surface. In one embodiment, the pan virtual button includes four arrows, and a direction and/or amount of panning depends on where in the pan virtual button a user presses. For example, pressing on a right facing arrow of the pan virtual button may cause panning to the right, pressing on an upward facing arrow may cause upward panning, and so on. In one embodiment, different swipe gestures within the rotate virtual button cause a particular rotation of the view of the 3D surface (e.g., of a virtual camera viewing the 3D surface). For example, a rightward swipe may cause a rotation about a vertical axis in the right direction. In one embodiment, a rightward swipe in the zoom virtual button causes a zoom in command, and a leftward swipe in the zoom virtual button causes a zoom out command. Alternatively, pressing on any of the virtual buttons shown in FIG. 7D causes one or more new virtual buttons associated with the selected viewing operation to be displayed.

In one embodiment, different gestures on the touchscreen cause different operations changing a view of a 3D surface. For example, the touchscreen may support multi-touch control. Dragging of a first number of fingers (e.g., one finger) of a user across the touchscreen may cause rotation of a three-dimensional surface on a display. Dragging of a second number of fingers (e.g., two fingers) of the user across the touchscreen may cause panning of the three-dimensional surface on the display. An inward pinching motion of a user's fingers on the touchscreen may cause zooming out of the three-dimensional surface on the display. An outward pinching motion of the user's fingers on the touchscreen may cause zooming in of the three-dimensional surface on the display.

Figure 8:
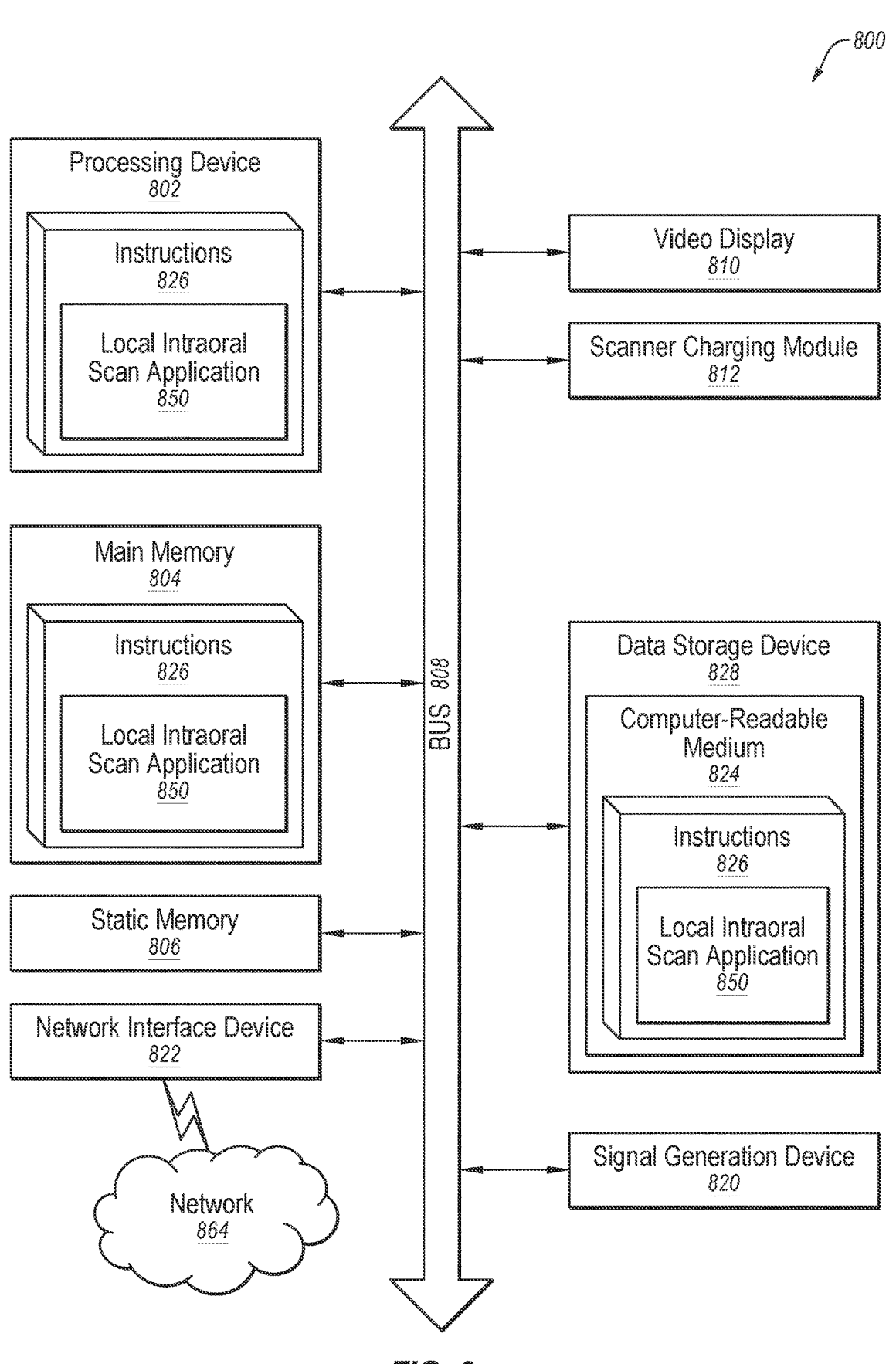
FIG. 8 illustrates a block diagram of an example computing device, in accordance with embodiments of the present disclosure.

FIG. 8 illustrates a diagrammatic representation of a machine in the example form of a computing device 800 within which a set of instructions, for causing the machine to perform any one or more of the methodologies discussed herein, may be executed. In one embodiment, computing device 800 corresponds to local device 105 of FIG. 1. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be, for example, a cradle and/or charging station for an intraoral scanner that includes an embedded system and/or SoC.

The example computing device 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory (e.g., a data storage device 828), which communicate with each other via a bus 808.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 826) for performing operations and steps discussed herein.

The computing device 800 may further include a network interface device 822 for communicating with a network 864. The computing device 800 also may include a video display unit 810 (e.g., a liquid crystal display (LCD) or a cathode ray tube (CRT)), and optionally a signal generation device 820 (e.g., a speaker).

The data storage device 828 may include a machine-readable storage medium (or more specifically a non-transitory computer-readable storage medium) 824 on which is stored one or more sets of instructions 826 embodying any one or more of the methodologies or functions described herein, such as instructions for local intraoral scan application 805. A non-transitory storage medium refers to a storage medium other than a carrier wave. The instructions 826 may also reside, completely or at least partially, within the main memory 804 and/or within the processing device 802 during execution thereof by the computer device 800, the main memory 804 and the processing device 802 also constituting computer-readable storage media.

The computer-readable storage medium 824 may also be used to store local intraoral scan application 850 or remote intraoral scan application (not shown), which may perform the operations described herein above. The computer readable storage medium 824 may also store a software library containing methods for the dental modeling logic 850. While the computer-readable storage medium 824 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

Figure 9:
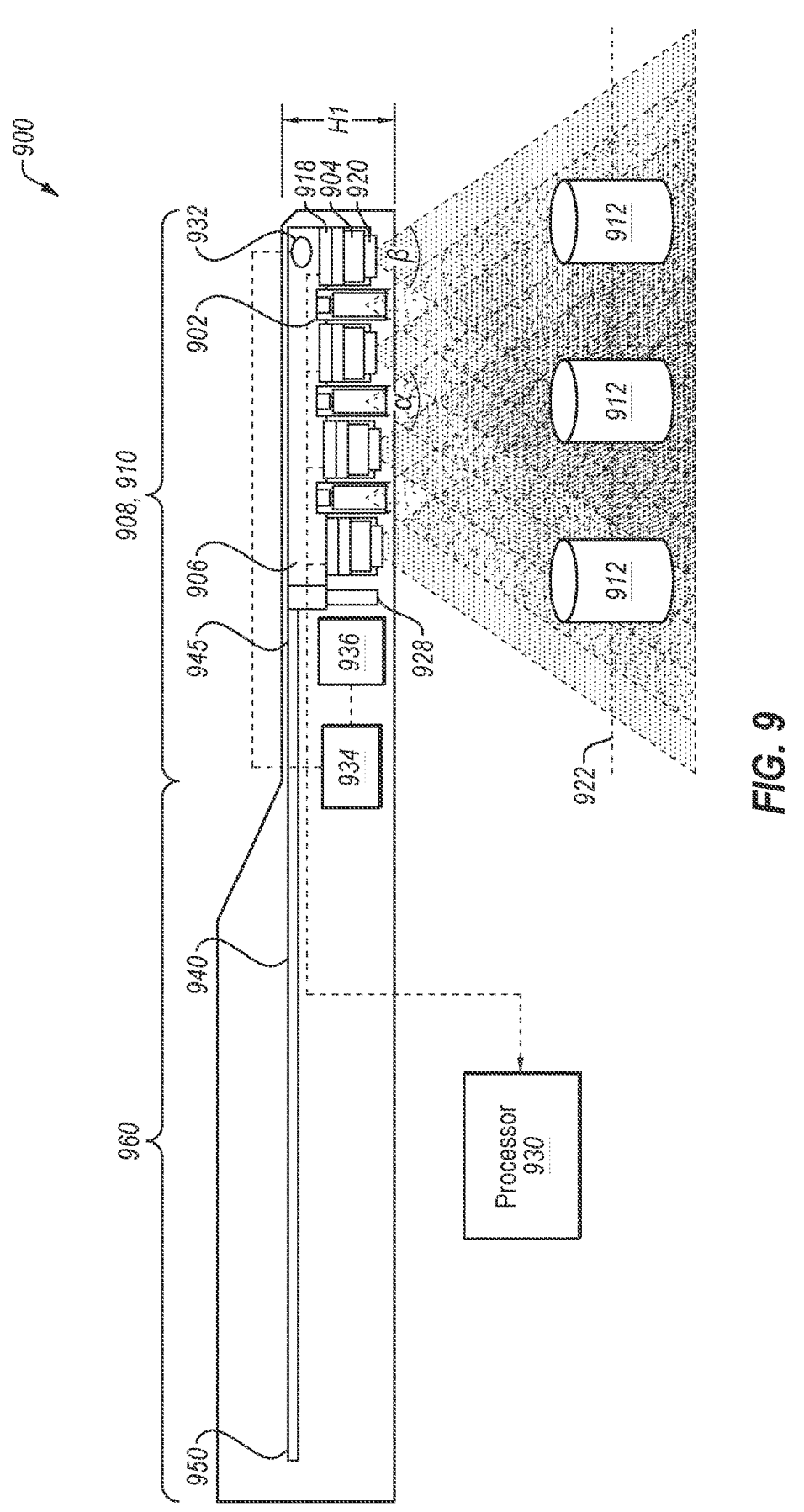
FIG. 9 illustrates an example intraoral scanner, in accordance with embodiments of the present disclosure.

Reference is now made to FIG. 9, which is a schematic illustration of an intraoral scanner 900 comprising an elongate handheld wand (e.g., a body with a probe at one end of the body), in accordance with some applications of the present disclosure. The intraoral scanner 900 may include a wireless module (not shown) disposed in a body of the intraoral scanner 900. The intraoral scanner 900 may correspond to intraoral scanner 150 of FIGS. 1A-B in embodiments. Intraoral scanner 900 includes a plurality of structured light projectors 902 and a plurality of cameras 904 that are coupled to a rigid structure 906 disposed within a probe 908 at a distal end 910 of the body of the intraoral scanner 900. In some applications, during an intraoral scanning procedure, probe 908 is inserted into the oral cavity of a subject or patient.

For some applications, structured light projectors 902 are positioned within probe 908 such that each structured light projector 902 faces an object 912 outside of intraoral scanner 900 that is placed in its field of illumination, as opposed to positioning the structured light projectors in a proximal end of the handheld wand and illuminating the object by reflection of light off a mirror and subsequently onto the object. Alternatively, the structured light projectors may be disposed at a proximal end of the handheld wand. Similarly, for some applications, cameras 904 and/or other optical sensors are positioned within probe 908 such that each camera 904 faces an object 912 outside of intraoral scanner 900 that is placed in its field of view, as opposed to positioning the cameras in a proximal end of the intraoral scanner and viewing the object by reflection of light off a mirror and into the camera. This positioning of the projectors and the cameras within probe 908 enables the scanner to have an overall large field of view while maintaining a low profile probe. Alternatively, the cameras may be disposed in a proximal end of the handheld wand.

In some applications, cameras 904 each have a large field of view R (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In one embodiment, a field of view (beta) for each camera is between 80 and 90 degrees, which may be particularly useful because it provided a good balance among pixel size, field of view and camera overlap, optical quality, and cost. Cameras 904 may include an image sensor 918 and objective optics 920 including one or more lenses. To enable close focus imaging, cameras 904 may focus at an object focal plane 922 that is located between 1 mm and 30 mm, e.g., between 4 mm and 24 mm, e.g., between 5 mm and 11 mm, e.g., 9 mm-10 mm, from the lens that is farthest from the sensor. In some applications, cameras 904 may capture images at a frame rate of at least 30 frames per second, e.g., at a frame of at least 75 frames per second, e.g., at least 100 frames per second. In some applications, the frame rate may be less than 200 frames per second.

A large field of view achieved by combining the respective fields of view of all the cameras may improve accuracy due to reduced amount of image stitching errors, especially in edentulous regions, where the gum surface is smooth and there may be fewer clear high resolution 3D features. Having a larger field of view enables large smooth features, such as the overall curve of the tooth, to appear in each image frame, which improves the accuracy of stitching respective surfaces obtained from multiple such image frames.

Similarly, structured light projectors 902 may each have a large field of illumination a (alpha) of at least 45 degrees, e.g., at least 70 degrees. In some applications, field of illumination a (alpha) may be less than 120 degrees, e.g., than 100 degrees.

For some applications, in order to improve image capture, each camera 904 has a plurality of discrete preset focus positions, in each focus position the camera focusing at a respective object focal plane 922. Each of cameras 904 may include an autofocus actuator that selects a focus position from the discrete preset focus positions in order to improve a given image capture. Additionally or alternatively, each camera 904 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the sensor.

In some applications, structured light projectors 902 and cameras 904 are coupled to rigid structure 906 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 922 that is located at least 4 mm from the lens that is farthest from the sensor. Due to different possible configurations of the projectors and cameras, some of the projected pattern may never be seen in the field of view of any of the cameras, and some of the projected pattern may be blocked from view by object 912 as the scanner is moved around during a scan.

Rigid structure 906 may be a non-flexible structure to which structured light projectors 902 and cameras 904 are coupled so as to provide structural stability to the optics within probe 908. Coupling all the projectors and all the cameras to a common rigid structure helps maintain geometric integrity of the optics of each structured light projector 902 and each camera 904 under varying ambient conditions, e.g., under mechanical stress as may be induced by the subject's mouth. Additionally, rigid structure 906 helps maintain stable structural integrity and positioning of structured light projectors 902 and cameras 904 with respect to each other.

For some applications, there is at least one uniform light projector 928 (which may be an unstructured light projector that projects light across a range of wavelengths) coupled to rigid structure 906. Uniform light projector 928 may transmit white light onto object 912 being scanned. At least one camera, e.g., one of cameras 904, captures two-dimensional color images of object 912 using illumination from uniform light projector 928. Light reflecting off of the object 912 may enter the scanner head and be received by the cameras. The cameras may then generate intraoral scan data based on the received light. The wireless communication module may wirelessly send the intraoral scan data to a local server computing device in embodiments.

A processor or processing device 930 of the local server computing device may run a surface reconstruction algorithm that may use detected patterns (e.g., dot patterns) projected onto object 912 to generate a 3D surface of the object 912. In some embodiments, the processor 930 may combine at least one 3D scan captured using illumination from structured light projectors 902 with a plurality of intraoral 2D images captured using illumination from uniform light projector 928 in order to generate a digital three-dimensional image of the intraoral three-dimensional surface. Using a combination of structured light and uniform illumination enhances the overall capture of the intraoral scanner and may help reduce the number of options that processor 930 needs to consider when running a correspondence algorithm used to detect depth values for object 912. In one embodiment, the intraoral scanner and correspondence algorithm described in U.S. application Ser. No. 16/446,181, filed Jun. 19, 2019, is used. U.S. application Ser. No. 16/446,181, filed Jun. 19, 2019, is incorporated by reference herein in its entirety. In embodiments, processor 930 may be a processor of local server computing device 105 of FIGS. 1A-B. Alternatively, processor 930 may be a processor integrated into the intraoral scanner 900.

For some applications, all data points taken at a specific time are used as a rigid point cloud, and multiple such point clouds are captured at a frame rate of over 10 captures per second. The plurality of point clouds are then stitched together using a registration algorithm, e.g., iterative closest point (ICP), to create a dense point cloud. A surface reconstruction algorithm may then be used to generate a representation of the surface of object 912.

For some applications, at least one temperature sensor 932 is coupled to rigid structure 906 and measures a temperature of rigid structure 906. Temperature control circuitry 934 disposed within handheld wand 900 (a) receives data from temperature sensor 932 indicative of the temperature of rigid structure 906 and (b) activates a temperature control unit 936 in response to the received data. Temperature control unit 936, e.g., a PID controller, keeps probe 908 at a target temperature (e.g., between 35 and 43 degrees Celsius, between 37 and 41 degrees Celsius, etc.). Keeping probe 908 above 35 degrees Celsius, e.g., above 37 degrees Celsius, reduces fogging of the glass surface of handheld wand 900, through which structured light projectors 902 project and cameras 904 view, as probe 908 enters the oral cavity, which is typically around or above 37 degrees Celsius. Keeping probe 908 below 43 degrees, e.g., below 41 degrees Celsius, prevents discomfort or pain.

In some embodiments, heat may be drawn out of the probe 908 via a heat conducting element 940, e.g., a heat pipe, that is disposed within handheld wand 900, such that a distal end 945 of heat conducting element 940 is in contact with rigid structure 906 and a proximal end 950 is in contact with a proximal end 960 of handheld wand 900. Heat is thereby transferred from rigid structure 906 to proximal end 960 of handheld wand 900. Alternatively or additionally, a fan disposed in a handle region of handheld wand 900 may be used to draw heat out of probe 908.

In one embodiment, intraoral scanner 150 corresponds to the intraoral scanner described in U.S. application Ser. No. 16/910,042, filed Jun. 23, 2020 and entitled "Intraoral 3D Scanner Employing Multiple Miniature Cameras and Multiple Miniature Pattern Projectors", which is incorporated by reference herein. In one embodiment, intraoral scanner 150 corresponds to the intraoral scanner described in U.S. application Ser. No. 16/446,181, filed Jun. 19, 2019 and entitled "Intraoral 3D Scanner Employing Multiple Miniature Cameras and Multiple Miniature Pattern Projectors", which is incorporated by reference herein.

In some embodiments, intraoral scanner 900 includes a touchscreen (not shown) disposed on the body of the intraoral scanner 900. The touchscreen may be configured to output a plurality of virtual buttons, to detect a touch input associated with a virtual button of the plurality of virtual buttons, and to provide a signal associated with the touch input of the virtual button to the processor of the local server computing device. In some embodiments, intraoral scanner 900 may receive an input from the local server computing device indicating a current mode of an intraoral scan application. Intraoral scanner 900 may then determine the plurality of virtual buttons to output on the touchscreen based on the current mode of the intraoral scan application and/or based on past inputs. Alternatively, the local server computing device may determine what virtual buttons are to be displayed on the touchscreen, and may provide data on what is to be displayed on the touchscreen to intraoral scanner 900.

In some embodiments an intraoral scanner that performs confocal focusing to determine depth information may be used.

Figure 10:
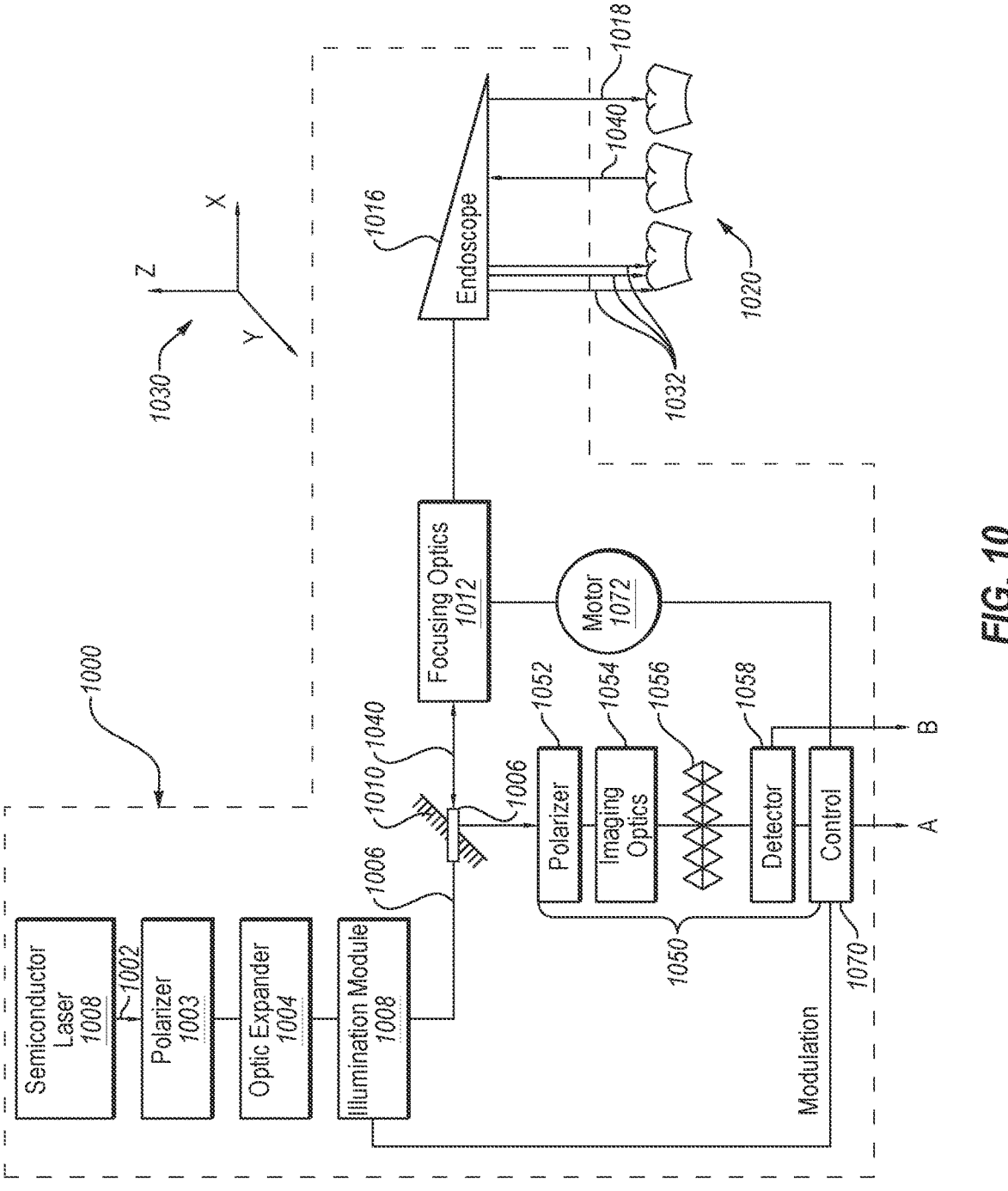
FIG. 10 illustrates another example intraoral scanner, in accordance with embodiments of the present disclosure.

FIG. 10 illustrates a functional block diagram of an intraoral scanner 1000 according to one embodiment. Intraoral scanner 1000 may correspond to intraoral scanner 150 of FIGS. 1A-B in embodiments. Together, the intraoral scanner 1000 and one or more local device (e.g., local device 105) may form a system for generating three dimensional surfaces and/or models of scanned intraoral objects. In one embodiment, the intraoral scanner is a confocal intraoral scanner. In one embodiment, intraoral scanner 1000 includes a touchscreen and a wireless communication module, as discussed above.

In one embodiment intraoral scanner 1000 includes a body comprising a probe at one end of the body. The probe includes a scanner head. The probe may include, for example, an endoscope 1016. Intraoral scanner 1000 includes a semiconductor laser unit 1008 in the body that emits focused light (e.g., a focused light beam), as represented by arrow 1002. The light 1002 passes through a polarizer 1003. Polarizer 1003 polarizes the light beam passing through polarizer 1003. Alternatively, polarizer 1003 may be omitted in some embodiments. The light then enters into an optic expander 1004 in the body that improves a numerical aperture of the light 1002. The light 1002 then passes through an illumination module 1008 in the body, which may split the light 1002 into an array of incident light beams 1006, represented here, for ease of illustration, by a single line. The illumination module 1008 may be, for example, a grating or a micro lens array that splits the light 1002 into an array of light beams 1006. In one embodiment, the array of light beams 1006 is an array of telecentric light beams. Alternatively, the array of light beams may not be telecentric.

The intraoral scanner 1000 further includes a unidirectional mirror or beam splitter (e.g., a polarizing beam splitter) 1010 in the body that passes the array of light beams 1006. A unidirectional mirror 1010 allows transfer of light from the semiconductor laser 1008 through to downstream optics, but reflects light travelling in the opposite direction. A polarizing beam splitter allows transfer of light (e.g., light beams) having a particular polarization and reflects light beams having a different (e.g., opposite) polarization. In one embodiment, the unidirectional mirror or beam splitter 1010 has a small central aperture. The small central aperture may improve a measurement accuracy of the intraoral scanner 1000. In one embodiment, as a result of a structure of the unidirectional mirror or beam splitter 1010, the array of light beams will yield a light annulus on an illuminated area of an imaged object as long as the area is not in focus. Moreover, the annulus will become a completely illuminated spot once in focus. This ensures that a difference between measured intensities of out-of-focus points and in-focus points will be larger.

Along an optical path of the array of light beams after the unidirectional mirror or beam splitter 1010 are focusing optics 1012 in the body, and an endoscopic probing member 46 at one end of the body. In one embodiment, the focusing optics are confocal focusing optics. Additionally, a quarter wave plate may be disposed along the optical path after the unidirectional mirror or beam splitter 1010 to introduce a certain polarization to the array of light beams. In some embodiments this may ensure that reflected light beams will not be passed through the unidirectional mirror or beam splitter 1010. Focusing optics 1012 may additionally include relay optics (not shown). Focusing optics 1012 may or may not maintain the same magnification of an image over a wide range of distances in the Z direction, wherein the Z direction is a direction of beam propagation (e.g., the Z direction corresponds to an imaging axis that is aligned with an optical path of the array of light beams 1006). The relay optics enable the intraoral scanner 1000 to maintain a certain numerical aperture for propagation of the array of light beams 1006.

The endoscopic probing member 1016 may include a rigid, light-transmitting medium, which may be a hollow object defining within it a light transmission path or an object made of a light transmitting material, e.g. a glass body or tube. In one embodiment, the endoscopic probing member 1016 include a prism such as a folding prism. At its end, the endoscopic probing member 1016 may include a mirror of the kind ensuring a total internal reflection. Thus, the mirror may direct the array of light beams towards a teeth segment 1020 or other intraoral object. The endoscope probing member 1016 thus emits light 1018 (e.g., an array of light beams), which impinges on to surfaces of the teeth section 1020.

The light 1018 (e.g., array of light beams) may be arranged in an X-Y plane, in the Cartesian frame 1030, propagating along the Z axis. As the surface on which the incident light hits is an uneven surface, illuminated points or locations 1032 are displaced from one another along the Z axis, at different $(X_i, Y_i)$ locations. Thus, while a point at one location may be in focus of the focusing optics 1012, points at other locations may be out-of-focus. Therefore, the light intensity of returned light (e.g., returned light beams) of the focused points will be at its peak, while the light intensity at other points will be off peak. Thus, for each illuminated point, multiple measurements of light intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. As pointed out above, the incident light from the light 1018 may form a light disk or a blurry image on the surface when out of focus and a complete light spot or a sharp image when in focus. Thus, the distance derivative will be larger when approaching in-focus position, increasing accuracy of the measurement.

The light scattered from each of the points may include a beam travelling initially in the Z axis along the opposite direction of the optical path traveled by the light beam 1018. Each returned light beam in an array of returning light beams 1040 may correspond to one of the incident light beams in array of light beams 1006. Given the asymmetrical properties of unidirectional mirror or beam splitter 1010, the returned light is reflected in the direction of detection optics 1050 in the body.

The detection optics 1050 may include a polarizer 1052 that has a plane of preferred polarization oriented normal to the plane polarization of polarizer 1003. Alternatively, polarizer 1003 and polarizer 1052 may be omitted in some embodiments. The array of returning light 1040 (e.g., array of returning light beams) may pass through imaging optics 1054 in one embodiment. The imaging optics 1054 may include one or more lenses. Alternatively, the detection optics 1050 may not include imaging optics 1054. In one embodiment, the returning light 1040 further passes through a matrix 1056, which may be an array of pinholes. Alternatively, no matrix 1056 is used in some embodiments. The returning light 1040 is then directed onto a detector 1058 in the body.

The detector 1058 is an image sensor having a matrix of sensing elements each representing a pixel of the image. If matrix 1056 is used, then each pixel further corresponds to one pinhole of matrix 1056. In one embodiment, the detector is a charge coupled device (CCD) sensor. In one embodiment, the detector is a complementary metal-oxide semiconductor (CMOS) type image sensor. Other types of image sensors may also be used for detector 1058. In one embodiment, the detector 1058 detects light intensity at each pixel.

In one embodiment, detector 1058 provides data to a local server computing device, such as local server computing device 105 of FIG. 1. Thus, each light intensity measured in each of the sensing elements of the detector 1058, is then captured and analyzed.

Intraoral scanner 1000 further includes a control module 1070 in the body connected both to semiconductor laser 1308 and a motor 1072, voice coil or other translation mechanism. In one embodiment, control module 1070 is or includes a field programmable gate array (FPGA) configured to perform control operations. Motor 1072 is linked to focusing optics 1012 for changing a focusing setting of confocal focusing optics 1012. This may adjust the relative location of an imaginary flat or non-flat focal surface of focusing optics 1042 along the Z-axis (e.g., in the imaging axis). Control module 1070 may induce motor 1072 to axially displace (change a location of) one or more lenses of the focusing optics 1012 to change the focal depth of the imaginary flat or non-flat focal surface. In one embodiment, motor 1072 or intraoral scanner 1000 includes an encoder (not shown) that accurately measures a position of one or more lenses of the focusing optics 1012. The encoder may include a sensor paired to a scale that encodes a linear position. The encoder may output a linear position of the one or more lenses of the focusing optics 1012. The encoder may be an optical encoder, a magnetic encoder, an inductive encoder, a capacitive encoder, an eddy current encoder, and so on. After receipt of feedback that the location of the one or more lenses has changed, control module 1070 may induce laser 1308 to generate a light pulse.

Processing logic of the local server computing device may determine the relative intensity in each pixel of a received intraoral scan over the entire range of focal settings of focusing optics 1012 from received intraoral scan data. Once a certain light point associated with a particular pixel is in focus, the measured intensity will be maximal for that pixel. Thus, by determining the $Z_i$ corresponding to the maximal light intensity or by determining the maximum displacement derivative of the light intensity, for each pixel, the relative position of each light point or spot along the Z axis can be determined for each pixel. Thus, data representative of the three-dimensional pattern of a surface in the teeth segment 1020 or other intraoral object can be obtained.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. An intraoral scanning system comprising:
   an intraoral scanner configured to generate intraoral scans and two-dimensional (2D) images during intraoral scanning; and
   a cradle for the intraoral scanner, the cradle comprising:
   a wireless module configured to wirelessly connect to the intraoral scanner; and
   a processing device to:
      receive the intraoral scans and the 2D images from the intraoral scanner;
      store the intraoral scans in a data storage of the cradle;
      output a subset of the 2D images to a display according to a first frame rate; and
      adaptively reduce the first frame rate during the intraoral scanning responsive to determining that one or more properties of a surface being scanned satisfy one or more criteria.

2. The intraoral scanning system of claim 1, further comprising:
   the display, wherein the display is one of a monitor, a television, a mobile device, or a desktop computer, and wherein the wireless module is to wirelessly connect with the display.

3. The intraoral scanning system of claim 1, wherein the processing device is to receive the 2D images at a second frame rate that is greater than the first frame rate.

4. The intraoral scanning system of claim 1, wherein the processing device is further to:

transmit the intraoral scans to a remote computing device via a network, wherein the remote computing device is to process the intraoral scans to generate a three-dimensional (3D) model of a patient's dental arch.

5. The intraoral scanning system of claim 1, wherein the first frame rate is about 1-10 frames per second.

6. The intraoral scanning system of claim 1, wherein the processing device is further to:

receive a command to enter a local three-dimensional (3D) rendering mode;

enter the local 3D rendering mode; and generate a 3D surface of a portion of a dental arch of a patient using a subset of the intraoral scans that is received after receipt of the command to enter the local 3D rendering mode.

7. The intraoral scanning system of claim 6, wherein a size of the 3D surface is limited by a 3D bounding shape around the portion of the dental arch.

8. The intraoral scanning system of claim 6, wherein the intraoral scanner comprises a touch screen, and wherein the touch screen is configured to present a virtual button that, when pressed, causes the command to enter the local 3D rendering mode to be sent to the processing device.

9. The intraoral scanning system of claim 6, wherein the processing device is further to:

exit the local 3D rendering mode responsive to an exit criterion being satisfied; and discard the 3D surface of the portion of the dental arch responsive to exiting the local 3D rendering mode.

10. The intraoral scanning system of claim 1, wherein the cradle comprises an additional processing device optimized for executing one or more trained machine learning models, and wherein the additional processing device is to use the one or more trained machine learning models to process at least one of the intraoral scans or the 2D images to identify at least one of excess tissue, moving tissue, hard tissue, or soft tissue.

11. The intraoral scanning system of claim 1, wherein the intraoral scanner comprises a touch screen, and wherein the touch screen is configured to present one or more virtual buttons that, when pressed, cause a command to adjust the first frame rate to be generated.

12. The intraoral scanning system of claim 1, wherein the intraoral scanner comprises a touch screen, and wherein the touch screen is configured to present one or more virtual buttons that, when pressed, cause a command to select a static first frame rate or an adaptive first frame rate to be generated.

13. The intraoral scanning system of claim 1, wherein the cradle further comprise the display that is to display the subset of the 2D images.

14. The intraoral scanning system of claim 13, wherein the display comprises a touch screen.

15. An intraoral scanning system comprising:

an intraoral scanner configured to generate intraoral scans and two-dimensional (2D) images during use; and a cradle for the intraoral scanner, the cradle comprising:

a wireless module configured to wirelessly connect to the intraoral scanner; and a processing device to:

receive the intraoral scans and the 2D images from the intraoral scanner;

store the intraoral scans in a data storage of the cradle;

output a subset of the 2D images to a display according to a first frame rate;

receive a command to enter a local three-dimensional (3D) rendering mode;

enter the local 3D rendering mode;

generate a 3D surface of a portion of a dental arch of a patient using a subset of the intraoral scans that is received after receipt of the command to enter the local 3D rendering mode;

determine at least one of a) a first amount of processing resources of the processing device that are being used or b) a second amount of the processing resources that are available;

determine that an exit criterion is satisfied responsive to at least one of a) the first amount of processing resources that are being used exceeding a first threshold or b) the second amount of processing resources that are available falling below a second threshold;

exit the local 3D rendering mode responsive to the exit criterion being satisfied; and discard the 3D surface of the portion of the dental arch responsive to exiting the local 3D rendering mode.

16. An intraoral scanning system comprising:

an intraoral scanner configured to generate intraoral scans and two-dimensional (2D) images during use; and a cradle for the intraoral scanner, the cradle comprising:

a wireless module configured to wirelessly connect to the intraoral scanner; and one or more processing device to:

receive the intraoral scans and the 2D images from the intraoral scanner;

store the intraoral scans in a data storage of the cradle;

output a subset of the 2D images to a display according to a first frame rate;

receive a command to enter a local three-dimensional (3D) rendering mode:

enter the local 3D rendering mode;

segment the intraoral scans into hard tissue and soft tissue using one or more trained machine learning models;

discard a part of the intraoral scans identified as soft tissue to reduce a computational load of generating a 3D surface of a portion of a dental arch of a patient; and subsequently generate the 3D surface of the portion of the dental arch of the patient using a subset of the intraoral scans that is received after receipt of the command to enter the local 3D rendering mode.

17. The intraoral scanning system of claim 16, wherein the one or more processing devices are to use a trained machine learning model to segment the intraoral scans.

18. An intraoral scanning system comprising:

an intraoral scanner configured to generate intraoral scans and two-dimensional (2D) images during use; and a cradle for the intraoral scanner, the cradle comprising:

a wireless module configured to wirelessly connect to the intraoral scanner; and a processing device to:

receive the intraoral scans and the 2D images from the intraoral scanner;

store the intraoral scans in a data storage of the cradle;

output a subset of the 2D images to a display according to a first frame rate; and adaptively change the first frame rate during intraoral scanning in accordance with a difficulty level associated with a portion of a dental arch being scanned.

19. The intraoral scanning system of claim 18, wherein the processing device is to set the first frame rate to a first value responsive to determining that the portion of the dental arch is associated with a first difficulty level, and is to set the first frame rate to a second value that is lower than the first value responsive to determining that the portion of the dental arch is associated with a second difficulty level that is greater than the first difficulty level.

20. The intraoral scanning system of claim 18, wherein the processing device is to determine the difficulty level based on processing of at least one of a) one or more most recent intraoral scans or b) one or more most recent 2D images.

21. The intraoral scanning system of claim 20, wherein the processing is performed by inputting at least one of the one or more most recent intraoral scans or the one or more most recent 2D images into a trained machine learning model that outputs the difficulty level.

* * * * *